US012678476B2

(12) United States Patent
Li et al.

(10) Patent No.: US 12,678,476 B2
(45) Date of Patent: Jul. 14, 2026

(54) METHODS OF MANUFACTURING INJECTABLE SUSTAINED RELEASE FORMULATIONS

(71) Applicant: Foresee Pharmaceuticals Co., Ltd., Taipei (TW)

(72) Inventors: Yuhua Li, Newark, DE (US); Andrew J. Guarino, Newark, DE (US)

(73) Assignee: FORESEE PHARMACEUTICALS CO., LTD., Taipei (TW)

( * ) Notice: Subject to any disclaimer, the term of this patent is extended or adjusted under 35 U.S.C. 154(b) by 370 days.

(21) Appl. No.: 18/554,849

(22) PCT Filed: Jun. 28, 2022

(86) PCT No.: PCT/US2022/035241
§ 371 (c)(1),
(2) Date: Oct. 11, 2023

(87) PCT Pub. No.: WO2023/278392
PCT Pub. Date: Jan. 5, 2023

(65) Prior Publication Data
US 2024/0390454 A1        Nov. 28, 2024

Related U.S. Application Data

(60) Provisional application No. 63/217,839, filed on Jul. 2, 2021.

(51) Int. Cl.
| | |
|---|---|
| *A61K 38/09* | (2006.01) |
| *A61K 9/00* | (2006.01) |
| *A61K 9/107* | (2006.01) |
| *A61K 47/22* | (2006.01) |
| *A61K 47/34* | (2017.01) |

(52) U.S. Cl.
CPC ............ *A61K 38/09* (2013.01); *A61K 9/0019* (2013.01); *A61K 9/107* (2013.01); *A61K 47/22* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,938,763 A | 7/1990 | Dunn et al. | |
| 5,278,201 A | 1/1994 | Dunn et al. | |
| 5,278,202 A | 1/1994 | Dunn et al. | |
| 5,324,519 A | 6/1994 | Dunn et al. | |
| 5,340,849 A | 8/1994 | Dunn et al. | |
| 5,487,897 A | 1/1996 | Polson et al. | |
| 5,599,552 A | 2/1997 | Dunn et al. | |
| 5,681,873 A | 10/1997 | Norton et al. | |

| | | | |
|---|---|---|---|
| 5,702,716 A | 12/1997 | Dunn et al. | |
| 5,733,950 A | 3/1998 | Dunn et al. | |
| 5,736,152 A | 4/1998 | Dunn | |
| 5,739,176 A | 4/1998 | Dunn et al. | |
| 5,744,153 A | 4/1998 | Yewey et al. | |
| 5,759,563 A | 6/1998 | Yewey et al. | |
| 5,780,044 A | 7/1998 | Yewey et al. | |
| 5,792,469 A | 8/1998 | Tipton et al. | |
| 5,945,115 A | 8/1999 | Dunn et al. | |
| 5,990,194 A | 11/1999 | Dunn et al. | |
| 6,143,314 A | 11/2000 | Chandrashekar et al. | |
| 6,261,583 B1 | 7/2001 | Dunn et al. | |
| 6,355,657 B1 | 3/2002 | Osborne | |
| 6,395,293 B2 | 5/2002 | Polson et al. | |
| 6,461,631 B1 | 10/2002 | Dunn et al. | |
| RE37,950 E | 12/2002 | Dunn et al. | |
| 6,528,080 B2 | 3/2003 | Dunn et al. | |
| 6,565,874 B1 | 5/2003 | Dunn et al. | |
| 8,173,148 B2 | 5/2012 | Dadey et al. | |
| 8,313,763 B2 | 11/2012 | Margaron et al. | |
| 9,744,207 B2 | 8/2017 | Li et al. | |
| 2011/0105389 A1 | 5/2011 | Hoveyda | |
| 2015/0126492 A1 | 5/2015 | Dechantsreiter et al. | |
| 2020/0390849 A1 | 12/2020 | Li et al. | |

FOREIGN PATENT DOCUMENTS

| | | |
|---|---|---|
| JP | 2021516253 A | 7/2021 |
| RU | 2728786 C2 | 7/2020 |
| WO | 2019125358 A1 | 6/2019 |

OTHER PUBLICATIONS

Russian Examination Report issued on Oct. 16, 2025 for related Russian Patent Application No. 2023133860/04 (074505).
Supplementary European Search Report issued on Mar. 25, 2025 for related EP Patent Application No. 22834035.2.
Wang Yan et al: "Influence of storage temperature and moisture on the performance of microsphere/hydrogel composites—ScienceDirect", International Journal of Pharmaceutics, [Online] vol. 454, No. 1, (Sep. 1, 2013), pp. 310-315, Retrieved from the Internet: URL:https://www.sciencedirect.com/science/article/pii/S0378517313005218?via=ihub>.
The International Search Report and the Written Opinion issued on Sep. 21, 2022 for related PCT/US2022/035241.
Office Action dispatched May 27, 2026 by Japanese Patent Office for Japanese Patent Application No. 2023-578075.

*Primary Examiner* — Anna R Falkowitz
*Assistant Examiner* — Edwin Coleman Mitchell
(74) *Attorney, Agent, or Firm* — MagStone Law, LLP; Enshan Hong

(57) ABSTRACT

The present application provides a method for the manufacture of a viscous liquid suspension or emulsion for controlled release drug delivery, where the composition comprises: a lactate-based polymer having a weight average molecular weight between 5,000 and 50,000 dalton; a biocompatible solvent; and a bioactive substance or a salt thereof. The method involves weighing, mixing, dissolving the raw materials, filtering the product, and degassing the product to produce a uniform formulation that can be accurately filled in a single ready to use syringe.

12 Claims, 5 Drawing Sheets

-980 mbar                              atmosphere

METHODS OF MANUFACTURING INJECTABLE SUSTAINED RELEASE FORMULATIONS

CROSS REFERENCE TO RELATED APPLICATION

This application is a U.S. national stage of international application No. PCT/US2022/035241 filed on Jun. 28, 2022, which claims the benefit of U.S. Provisional Patent Application No. 63/217,839 filed on Jul. 2, 2021, the disclosure of which is incorporated herein by reference in its entirety.

BACKGROUND OF THE INVENTION

1. Field of the Invention

The field of the invention relates to a method for obtaining an injectable biodegradable delivery system for the sustained release delivery of bioactive substances. More particularly, the invention relates to a method for making a viscous liquid suspension or emulsion formulation containing a bioactive substance in a biodegradable polymer solution with a biocompatible solvent, which can be accurately filled into a single ready to use syringe.

2. Description of the Related Art

Biocompatible and biodegradable polymers have been increasingly used as drug delivery carriers to provide sustained, or delayed, release of bioactive substances to achieve long-acting therapeutic effects. The delivery systems are available in various injectable depot forms including liquid forms, suspensions, emulsions, solid implants, microspheres, microcapsules, and microparticles.

Sustained release delivery systems using biocompatible and biodegradable polymers are particularly beneficial for highly potent drugs with a short half-life. Such delivery systems could reduce the frequency of administration and pain, enhance patient compliance, improve patient convenience, and lower the cost. For many bioactive substances, particularly hormones, they need to be delivered continuously at a controlled rate over a long period of time, and thus a controlled release delivery system is highly desirable. Such systems may be provided by incorporating the bioactive substances in biodegradable and biocompatible polymer matrices. In one approach, the polymer is dissolved in an organic solvent and then mixed with the bioactive substance that is fabricated into the forms of microparticles, microspheres, microcapsules, microgranules, or solid implants by removing the organic solvent. The bioactive substance is entrapped within the solid polymer matrices. Several products have been successfully developed by using biodegradable polymers in the forms of microparticles and solid implants, such as Lupron Depot, Trelstar, Sandostatin LAR, etc. Although these products are effective, they have drawbacks and limitations, such as the large volume of suspending fluids for microparticles, or surgical insertion for solid implants, such as Zoladex. These products are not very user and patient friendly. In addition, the manufacturing methods for producing sterile products reproducibly are complicated, resulting in high cost of manufacturing. It is highly desirable that a composition can be easily manufactured and used.

In another approach, the biodegradable polymer and bioactive substances are dissolved in a biocompatible solvent to provide a liquid or flowable composition. When the liquid composition is injected into the body, the solvent dissipates into the surrounding aqueous environment, and the polymer precipitates to form a solid or gel depot from which the bioactive substance is released over a long period of time. The following references U.S. Pat. Nos. 8,173,148; 8,313, 763; 6,565,874; 6,528,080; RE37,950; 6,461,631; 6,395, 293; 6,355,657; 6,261,583; 6,143,314; 5,990,194; 5,945, 115; 5,792,469; 5,780,044; 5,759,563; 5,744,153; 5,739, 176; 5,736,152; 5,733,950; 5,702,716; 5,681,873; 5,599, 552; 5,487,897; 5,340,849; 5,324,519; 5,278,202; 5,278, 201; and 4,938,763 are believed to be representative in this area and are incorporated herein by reference. Notwithstanding some success, those methods are not entirely satisfactory for a large number of bioactive substances that would be effectively delivered by such an approach.

SUMMARY OF THE INVENTION

The present application discloses a method for obtaining an injectable biodegradable delivery system for the sustained release delivery of bioactive substances with improved characteristics. The use of a salt of a bioactive substance formed with a strong acid in a formulation with a biodegradable polymer and a biocompatible solvent improves the stability of the formulation and can minimize the generation of bioactive substance related impurities and undesirable premature degradation of the biodegradable polymer. This improved stability allows it to be stored in a single ready to use syringe. It can be injected into patients directly to form a sustained release depot. However, due to the uniqueness of this type of formulation, there is no known method for manufacturing this type of formulation. It was unexpectedly found that after mixing these materials together, the resulting solution became a liquid suspension or emulsion that had liquid droplets of the bioactive substance suspended in the biodegradable polymer solution. These droplets could vary greatly in size depending on the manufacturing method, resulting in a non-uniform formulation. In addition, the mixing method generates air bubbles, which are difficult to remove due to the high viscosity and elasticity of the formulation resulting from the molecular weight of the polymer as well as the concentrations of the polymer and bioactive substance in the formulation. The solubilization of the biodegradable polymer and bioactive substance also generates many microbubbles in the resulting viscous suspension or emulsion. The majority of these bubbles have to be removed prior to filling into syringes in order to accurately measure the fill volume for accurate dosing. Therefore, there is a need to develop a method to manufacture a uniform formulation that can deliver a bioactive substance from a biodegradable polymer solution that can be accurately filled in a single ready to use syringe.

It was unexpectedly discovered that a formulation made by mixing the peptide salt of a strong acid with a biodegradable polymer in a biocompatible solvent is a liquid suspension or emulsion that has liquid droplets of the bioactive substance (bioactive substance rich phase) suspended in the biodegradable polymer solution (polymer rich continuous phase). These bioactive substance rich liquid droplets in the polymer solution continuous phase can vary in size and size distribution depending on the manufacturing method. This variability in droplet size may lead to performance issues or stability issues for the formulation. The variability in droplet size distribution can also lead to inhomogeneity issues and dosing inconsistencies. This formulation may be difficult to accurately fill into syringes due to the high viscosity of the formulation and high amount of trapped air bubbles introduced into the formulation during the manufacturing process. Thus, a need exists for a method to manufacture this type of formulation so that it is uniform and stable and can be accurately filled into a single ready to use syringe.

The present application describes a manufacturing method for a sustained release formulation that can be filled into a single syringe that is uniform and stable. The present application provides a method to combine the biodegradable polymer, the biocompatible solvent, and the bioactive substance, followed by degassing and/or filtrating the resulting formulation, in order to accurately fill the formulation into a single, ready to use syringe. More specifically, the present application describes a method to manufacture a formulation in a single, ready to use syringe for the sustained delivery of a bioactive substance from a biodegradable polymer composition.

The method in accordance with the present application comprises a) combining the biodegradable polymer and a biocompatible solvent with a bioactive substance; b) degassing the formulation; and c) optionally filtering the resulting formulation. This method results in a stable and uniform formulation that can be accurately pre-filled into a single syringe, providing a ready to use system.

The bioactive substances of the present application can be in the form of a peptide, prodrug, or salt thereof that is capable of providing a biological, physiological, or therapeutic effect. The bioactive substance can be dissolved or suspended in the biodegradable polymer and biocompatible solvent to form a viscous liquid suspension or emulsion having a viscosity greater than 10,000 centipoise (cPs). The viscosity can range from 10,000 to 100,000 cPs. Upon injection of the viscous liquid suspension, the bioactive substance is released over time by diffusion and degradation of the implant.

According to the present application, the biocompatible solvent may be selected from a group consisting of N-methyl-2-pyrrolidone (NMP), 2-pyrrolidone, methoxy-polyethylene glycol, alkoxypolyethylene glycol, polyethylene glycol esters, glycofurol, glycerol formal, methyl acetate, ethyl acetate, methyl ethyl ketone, dimethylformamide (DMF), dimethylsulfoxide (DMSO), dimethylacetamide (DMAC), tetrahydrofuran (THF), caprolactam, decylmethylsulfoxide, benzyl alcohol, benzyl benzoate, ethyl benzoate, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, ethyl lactate, propylene carbonate, ethylene carbonate, butyrolactone, and 1-dodecylazacyclo-heptan-2-one, and combinations thereof.

According to the present application, the biodegradable polymer may be a linear polymer, or a branched polymer, or a mixture of the two. Preferably, the polymer is a lactate-based polymer. The lactate-based polymer includes homopolymers of lactic acid or lactide monomers (poly (lactic acid) or polylactide, PLA), and copolymers of lactic acid (or lactide) with other monomers (for example, glycolic acid, glycolide (poly(lactide-co-glycolide), PLG or PLGA) and the like). The weight average molecular weight of the polymer is typically 5,000 to 50,000. The polymer would ideally have an acid number of less than 3 mgKOH/g, preferably less than 2 mgKOH/g, and more preferably less than 1 mgKOH/g.

This polymer, when formulated with the bioactive substance and the biocompatible solvent would form a stable suspension or emulsion, which can be prefilled into a single syringe. According to the present application, an injectable composition for controlled release drug delivery can be produced by a method comprising: the methods of compounding and mixing of raw materials, followed by filtration and degassing of the product, in order to accurately fill the formulation in a single, ready to use syringe.

According to the present application, the mixing, filtration, and degassing are performed under controlled humidity of less than 60%, preferably less than 40% at room temperature under nitrogen, argon or dry air. The materials can be mixed in any order, but may be done in a way to minimize the mixing time and to prevent material from clumping while maintaining the product temperature.

According to the present application, the formulation is filtered by applying an inlet pressure of 1 bar to 10 bars and a suitable vacuum on the outlet side. The vacuum is between −300 mbar to −1000 mbar. The average pore size of the filter is between 10 to 150 µm, preferably 20 to 100 µm, more preferably 25 µm, 30 µm, 40 µm, 50 µm, 60 µm, 70 µm, 80 µm. The filter can be made from polymer, such as polypropylene or Teflon, or metal, such as aluminum or stainless steel. The filtration step can be performed before or after the degassing step. The degassing is performed under a final vacuum of 75% to 99.9% or a relative vacuum pressure of −300 mbar to −1000 mbar. The degassing may be performed step wise in order to minimize the product expansion and the time of this expansion, which can affect the uniformity of the product due to the change in viscosity on expansion. The degassing may result in a product that is almost free of bubbles, or has a minimal number of bubbles at the surface of the product.

Specifically, according to one aspect of the present application, a method of manufacturing an injectable sustained release formulation comprises:

i. a compounding step that is conducted under a controlled humidity of less than 60% at 15-25° C., wherein the compounding step comprises a) introducing ≥70% of a total amount of the NMP into a compounding vessel; b) dividing the biodegradable polymer into multiple fractions and adding a first fraction of the biodegradable polymer to the compounding vessel, and mixing the first fraction of the biodegradable polymer with the NMP in the compounding vessel until the first fraction of the biodegradable polymer is wetted or dissolved, then separately and sequentially introducing each of remaining fraction(s) of the biodegradable polymer to the compounding vessel and mixing until newly added fraction of the biodegradable polymer is wetted or dissolved before introducing a next fraction of the biodegradable polymer; c) after all the fractions of the biodegradable polymer are dissolved or substantially dissolved, adding the LHRH agonist in 1 to 20 fractions separately and sequentially into the compounding vessel and mixing the fraction of LHRH agonist with the NMP and biodegradable polymer in the compounding vessel until the LHRH agonist is wetted or dissolved, wherein a subsequent fraction of the LHRH agonist, if any, is added after the LHRH agonist previously added into the compounding vessel is wetted or dissolved, and mixing the LHRH agonist with the NMP and biodegradable polymer in the compounding vessel to form the formulation; and ii. a degassing step that is performed by four (4) or more vacuum/vent cycles of applying a relative vacuum pressure between −300 mbar and −1000 mbar to the compounding vessel or a degassing vessel containing the formulation prepared in (i) above, maintaining the vacuum for a time period between 5 min and 720 min, and releasing the vacuum to allow venting; wherein the vacuum level maintained at each vacuum/vent cycle is at least as strong as or stronger than that maintained in an immediately previous cycle.

The formulation may be a viscous suspension or emulsion of LHRH agonist rich phase (LHRH/NMP droplets) having a droplet diameter of Dv50 of less than 50 μm suspended in a biodegradable polymer rich continuous phase and has a viscosity of greater than 10,000 centipoises (cPs). The injectable sustained release formulation may comprise a luteinizing hormone releasing hormone (LHRH) agonist or a salt thereof, an N-methylpyrrolidone (NMP), and a biodegradable polymer.

DESCRIPTION OF PREFERRED EMBODIMENTS

Figure 1:
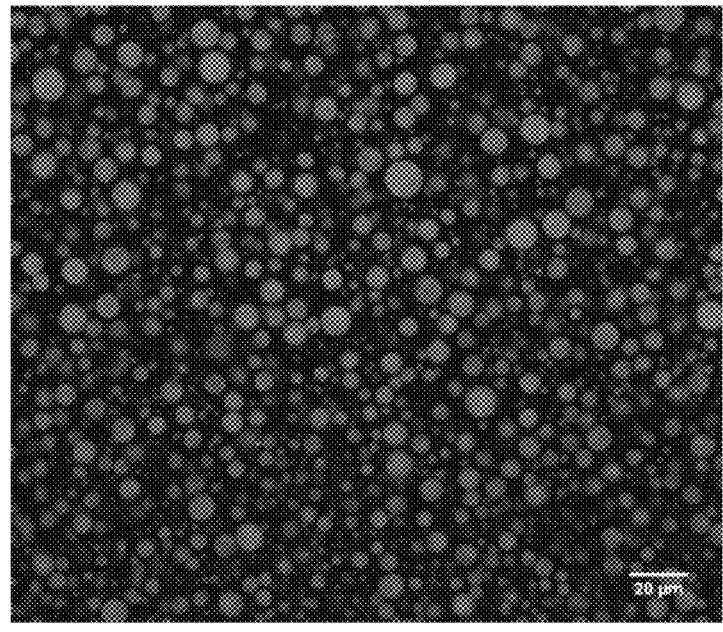
FIG. 1 is an image of leuprolide mesylate 50 mg drug product using inverted confocal microscope based on an embodiment of the present invention.

The present application provides the method of manufacturing an injectable polymeric formulation for the sustained release delivery of bioactive substances. The injectable polymeric compositions of the present application comprise a) a bioactive substance or salt thereof; b) a biocompatible solvent; and c) a biodegradable homopolymer or copolymer. The injectable polymeric composition can be prefilled into a single syringe through a specific method of the current application. The method comprises weighing and mixing the raw materials, as well as filtering and degassing the product, allowing for accurately filling the formulation into a syringe to form a product kit in a ready to use configuration.

The formulation of the present application is in the form of a viscous liquid suspension or emulsion, which moves as a fluid so that it may be injected through a needle, cannula, tube, laparoscope, probe, or other delivery device. When administered to a subject, such an injectable composition forms a depot in-situ from which the controlled release of the bioactive substance can be sustained for a desired period of time depending upon the composition. The depot or implant may be a solid, a gel, a paste, a semisolid, or a viscous liquid. With the proper selections of the biodegradable polymer and other components, the duration of the sustained release of the bioactive substance can be controlled over a period of time from several weeks to one year.

The injectable polymeric composition of the present application may also include non-polymeric compounds, and/or additives for controlling release, such as rate release modulating agents, pore forming agents, plasticizers, organic solvents, encapsulation agents for encapsulating the bioactive substance, thermal gelling agents, burst effect reducing materials, hydrogels, polyhydroxyl materials, leaching agents, tissue transporting agents, or other similar additives or any combination thereof.

The terms "a", "an" and "one", as used herein, are meant to be interpreted as "one or more" and "at least one."

As used herein, in the context of the present application, all numbers disclosed herein are approximations, whether or not the words "about" or "approximately" are used. Each numerical number means a range of the numerical value ±10% of the numerical value unless otherwise indicated. For example, "about 100 mg" or "100 mg" includes any values between 90 and 110 mg.

The term "room temperature" as used herein is defined as 15-25° C.

The term "sustained or controlled release delivery", as defined herein, is intended to refer to the delivery of a bioactive substance in vivo over a desired, extended period of time following administration, preferably from at least a few days to one year.

The term "bioactive substance" is meant to include any materials having diagnostic and/or therapeutic properties including, but not limited to, organic small molecules, inorganic small molecules, macromolecules, peptides, oligopeptides, proteins, or enzymes, nucleotides, nucleosides, oligonucleotides, oligonucleosides, polynucleotides, polynucleotides, polynucleic acids or similar molecules constitute such chemical compounds. Non-limiting examples of therapeutic properties are antimetabolic, antifungal, anti-inflammatory, antitumoral, antiinfectious, antibiotics, nutrient, agonist, and antagonist properties.

The bioactive substances of the present application may be in the form of a free molecule, an organic or inorganic salt of the free molecule, or it may be complexed or covalently conjugated with a carrier agent, may be a pro-drug, or may be a multiform bioactive substance (multiple units of the bioactive substance either complexed or covalently bonded together).

The term "peptide" as used herein is in a generic sense to include poly(amino acids) that are normally generally referred to as "peptides", "oligopeptides", and "polypeptides" or "proteins" which are used interchangeably herein. The term also includes bioactive peptide analogs, derivatives, acylated derivatives, glycosylated derivatives, pegylated derivatives, fusion proteins and the like. The term "peptide" is meant to include any bioactive peptides having diagnostic and/or therapeutic properties including, but not limited to, antimetabolic, antifungal, anti-inflammatory, antitumoral, antiinfectious, antibiotics, nutrient, agonist, and antagonist properties. The term also includes synthetic analogues of peptides, unnatural amino acids having basic functionality, or any other form of introduced basicity.

The preferred peptides used herein include Luteinizing hormone-releasing hormone (LHRH), and LHRH agonists such as leuprorelin or leuprolide, buserelin, gonadorelin, deslorelin, fertirelin, histrelin, lutrelin, goserelin, nafarelin, triptorelin, and antagonists such as cetrorelix, enfuvirtide, thymosin α1, degarelix, abarelix.

The bioactive substance used in the present application may be itself or a biocompatible organic salt. The acid used to form the biocompatible organic salt of the bioactive substance preferably has a pKa less than 5. The acids suitable for the present application may be selected from, but not limited to, the group consisting of hydrochloric acid, hydrobromic acid, nitric acid, chromic acid, sulfuric acid, methanesulfonic acid, trifluromethane sulfonic acid, trichloroacetic acid, dichloroacetic acid, bromoacetic acid, chloroacetic acid, cyanoacetic acid, 2-chloropropanoic acid, 2-oxobutanoic acid, 2-chlorobutanoic acid, 4-cyanobutanoic acid, pamoic acid, perchloric acid, phosphoric acid, hydrogen iodide, acetic acid, 2,2-dichloroacetic acid, adipic acid, alginic acid, L-ascorbic acid, L-aspartic acid, benzenesulfonic acid, benzoic acid, 4-acetamido benzoic acid, (+)-camphoric acid, (+)-camphor-10-sulfonic acid, capric acid, (decanoic acid), caproic acid (hexanoic acid), caprilic acid (octanoic acid)carbonic acid, cinnamic acid, citric acid, cyclamic acid, decanoic acid, dodecylsulfuric acid, ethane-1,2-disufonic acid, ethanesulfonic acid, 2-hydroxy-ethane-sulfonic acid, formic acid, fumaric acid, galactic acid, gentisic acid, D-glucoheptonic acid, D-gluconic acid, D-glucuronic acid, glutamic acid, glutaric acid, 2-oxo-glutaric acid, glycerophosphoric acid, glycolic acid, hippuric acid, isobutyric acid, DL-lactic acid, lactobionic acid, lauric acid, maleic acid, (−)-L-malic acid, malonic acid, DL-mandelic acid, muric acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, embonic acid, proprionic acid, (−)-L-pyroglutamic acid, salicyclic acid, 4-amino-salicylic acid, sebacic acid, stearic acid, succinic acid, (+)-L-tartaric acid, thiocyanic acid, p-toluenesulfonic acid, undecylenic acid. The selection of the suitable acids is well-known to those of skill in the art.

The term "strong acid", as defined herein, is meant to include any acids with a pKa less than 3, and preferably less than 0. The strong acids suitable for the present application may be selected from, but not limited to, the group consisting of hydrochloric acid, hydrobromic acid, nitric acid, chromic acid, sulfuric acid, methanesulfonic acid, trifluromethane sulfonic acid, toluenesulfonic acid (p), trichloroacetic acid, dichloroacetic acid, bromoacetic acid, chloroacetic acid, cyanoacetic acid, 2-chloropropanoic acid, 2-oxobutanoic acid, 2-chlorobutanoic acid, 4-cyanobutanoic acid, pamoic acid, perchloric acid, phosphoric acid, hydrogen iodide, and the like.

The "weak acid", as defined herein, is meant to include any acids with a pKa greater than 3. The weak acids suitable for the present application may be selected from, but not limited to, the group consisting of 1-hydroxy-2-naphthoic acid, 2-oxoglutaric acid, 4-acetamidobenzoic acid, 4-aminosalicylic acid, acetic acid, adipic acid, ascorbic acid (L), aspartic acid (L), benzoic acid, camphoric acid (+), capric acid (decanoic acid), caproic acid (hexanoic acid), caprylic acid (octanoic acid), carbonic acid, cinnamic acid, citric acid, formic acid, fumaric acid, galactaric acid, gentisic acid, glucoheptonic acid (D), gluconic acid (D), glucuronic acid (D), glutamic acid, glutaric acid, glycolic acid, hippuric acid, isobutyric acid, lactic acid (DL), lactobionic acid, lauric acid, maleic acid, malic acid (−L), malonic acid, mandelic acid (DL), oleic acid, oxalic acid, palmitic acid, proprionic acid, pyroglutamic acid (−L), salicylic acid, sebacic acid, stearic acid, succinic acid, tartaric acid (+L), thiocyanic acid, undecylenic acid, and the like.

The biocompatible organic salt of the bioactive substance can be prepared by simple acid and base titration or neutralization. The biocompatible organic salt of the bioactive substance can be prepared during its synthesis and purification methods. Alternatively, the salts can be prepared from bioactive substance in the form of a free base. The free base is dissolved in a suitable liquid medium. This solution of the bioactive substance is mixed with a solution of an acid to form the beneficial salts by removing the solvent through suitable means, such as filtration, precipitation, or lyophilization. If the bioactive substance is in its common commercially available salt form, a different salt can be obtained by using a simple salt exchange method or ion-exchange method such as lyophilization, precipitation or other methods known in the art. For example, leuprolide acetate is dissolved in a suitable liquid medium, e.g., water. This solution of the peptide is mixed with an aqueous solution of a strong acid, such as methanesulfonic acid. When the leuprolide acetate and a strong acid, such as methanesulfonic acid are dissolved in water, the peptide tends to be associated with mesylate ion, as the stronger methanesulfonic acid displaces the weaker carboxylic acetic acid. The solvent and liberated acetic acid (or other weak but volatile carboxylic acid) may be removed under vacuum. Thus, the mixture solution is freeze-dried to remove water and the weaker acid to form the desired salts. If the bioactive substance is not stable under low pH, the biocompatible organic salts of the bioactive substance can be prepared through extensive dialysis against very low concentration of an acid.

The polymer compositions of the present application may contain bioactive substance in a range of 0.01 to 40% by weight. In general, the optimal drug loading depends upon the period of release desired and the potency of the bioactive substance. Obviously, for bioactive substance of low potency and longer period of release, higher levels of incorporation may be required.

The biocompatible solvents of the present application may be miscible or dispersible in aqueous or body fluid. The term "dispersible" means that the solvent is partially soluble or miscible in water. A single solvent or a mixture of solvents may have a solubility or miscibility in water of greater than 0.1% by weight. Preferably, the solvent has a solubility or miscibility in water of greater than 3% by weight. More preferably, the solvent has a solubility or miscibility in water of greater than 7% by weight. The suitable biocompatible solvent may be able to diffuse into body fluid so that the liquid composition coagulates or solidifies. Single and/or mixture of such solvents can be employed; the suitability of such solvents can be determined readily by simple experimentations.

Examples of biocompatible solvent include, but are not limited to, N-methyl-2-pyrrolidone (NMP), 2-pyrrolidone, methoxypolyethylene glycol, alkoxypolyethylene glycol, polyethylene glycol esters, glycofurol, glycerol formal, methyl acetate, ethyl acetate, methyl ethyl ketone, dimethylformamide (DMF), dimethylsulfoxide (DMSO), dimethylacetamide (DMAC), caprolactam, decylmethylsulfoxide, benzyl alcohol, benzyl benzoate, ethyl benzoate, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, ethyl lactate, propylene carbonate, ethylene carbonate, butyrolactone, and 1-dodecylazacyclo-heptan-2-one, and combinations thereof. Preferred biocompatible solvents include N-methyl-2-pyrrolidone (NMP), 2-pyrrolidone, dimethyl-sulfoxide, dimethylacetamide (DMAC), glycofurol, glycerol formal, benzyl alcohol, benzyl benzoate, methoxypolyethylene glycol, alkoxypolyethylene glycol, polyethylene glycol esters, and isopropylidene glycol.

The solubility of the biodegradable polymers in various organic solvents will differ depending upon the characteristics of the polymers and their compatibility with the solvents. Thus, the same polymer will not be soluble to the same extent in different solvents. For example, PLGA has a much higher solubility in N-methyl-2-pyrrolidone (NMP) than that in triacetin. However, when PLGA solution in NMP is in contact with aqueous solution, NMP will dissipate very rapidly to form a solid polymer matrix due to its high water miscibility. The fast diffusion rate of the solvent may result in a solid implant forming quickly, however, it may also lead to a high initial burst release. When PLGA solution in triacetin is in contact with aqueous solution, triacetin will dissipate very slowly due to its low water miscibility. The slow diffusion rate of the solvent may take a long time to transform from a viscous liquid to a solid matrix. There may be an optimum balance at which the solvent diffuses out and the coagulation of the polymer to encapsulate peptide substances. Therefore, it may be advantageous to combine different solvents to obtain a desirable delivery system. The solvents of low and high water miscibility may be combined to improve the solubility of the polymer, modify the viscosity of the composition, optimize the diffusion rate, and reduce the initial burst release.

The polymeric compositions of the present application typically contain a biocompatible solvent in a range of 10% to 99% by weight. The viscosity of the polymeric compositions of the application depends on the molecular weight of the polymer and biocompatible solvent used. The viscosity can range from 10,000 to 100,000 cPs. Preferably the concentration of the polymer in the compositions is less than 70% by weight. More preferably the concentration of the polymer in the compositions is less than 60% by weight.

A "polymer" is a large molecule, or macromolecule, composed of many repeated subunits. Polymers range from familiar synthetic plastics such as polystyrene to natural biopolymers such as DNA and proteins that are fundamental to biological structure and function. Polymers, both natural and synthetic, are created via polymerization of many small molecules, known as monomers. Polymerization is the method of combining many small molecules known as monomers into a covalently bonded chain or network. The polymer large molecular mass relative to small molecule compounds produces unique physical properties, including toughness, viscoelasticity, and a tendency to form glasses and semicrystalline structures rather than crystals.

The term "biodegradable" refers to a material that gradually decomposes, dissolves, hydrolyzes and/or erodes in situ. Generally, the "biodegradable polymers" herein are polymers that are hydrolyzable, and/or bioerode in situ primarily through hydrolysis and/or enzymolysis.

The term "biodegradable polymer" as used herein is meant to include any biocompatible and/or biodegradable synthetic and natural polymers that can be used in vivo. Generally, the biodegradable polymer of the present application may be a linear polymer, or a branched or star polymer, or a mixture of a linear polymer and a branched and/or star polymer. Preferably, the biodegradable polymer of the present application is lactate-based polymer. The "lactate-based polymer" as used herein is a polymer that contains a lactate unit in the polymer.

Lactate-based polymers include any homopolymers/copolymers that contain lactate, lactic acid, or lactide monomers. The lactate-based polymer of the present application includes homopolymers of lactic acid or lactide monomers (poly(lactic acid) or polylactide, PLA), and copolymers of lactic acid (or lactide) with other monomers (for example, glycolic acid (or glycolide) (poly(lactide-co-glycolide), PLG or PLGA) and the like). The lactate-based polymer may have the same end groups, i.e., all the end groups are the same, such as ester, or hydroxyl or carboxylic acid. The lactate-based polymer may have mixed end groups of ester, hydroxyl, and/or carboxylic acid. The lactate-based polymer can have a diol core with end hydroxyl groups, such as those examples disclosed in U.S. Pat. No. 8,470,359. Similarly, the lactate-based polymer may have a triol or polyol core, such as glucose, with end hydroxyl groups. The lactate-based polymer may have one end group as an ester and the other end with a hydroxyl group or carboxylic acid group. The lactate-based polymer may also have one end hydroxyl group and the other end with a carboxylic acid or an ester, or vice versa.

The lactate-based polymer of the present application has a weight-average molecular weight of usually from 5,000 to 50,000. The lactate-based polymer of the present application may be a commercially available product or a polymer prepared by a known method. The type, molecular weight, and amount of biodegradable polymer present in the compositions can influence the length of time in which the bioactive substance is released from the controlled release implant. The more lactide in the polymer, the longer the degradation time of the polymer. The larger the molecular weight of the polymer, the longer the degradation time.

The lactate-based polymer of the present application also includes block copolymers, such as A-B-A block copolymers, B-A-B block copolymers, and/or A-B block copolymers and/or branched copolymers. The preferred block copolymers are those wherein the A block comprises a lactate-based polymer and the B block comprises a polymer selected from polyglycolides, poly(lactide-co-glycolide)s, polyanhydrides, poly(ortho ester)s, polyetheresters, poly-caprolactones, polyesteramides, poly(ε-caprolactone)s, poly(hydroxybutyric acid)s, and blends and copolymers thereof. The B block can also be a polyethylene glycol or mono-functionally derivatized polyethylene glycol, such as methoxy polyethylene glycol. Some of these combinations may form acceptable thermal reversible gels.

According to the present application, the lactate-based polymers have a weight-average molecular weight of from 5,000 to 50,000, 5,000 to 45,000, 5,000 to 40,000, 5,000 to 35,000, 5,000 to 30,000, 5,000 to 25,000, 5,000 to 20,000, 5,000 to 15,000, 5,000 to 12,000, or 10,000 to 40,000, or 12,000 to 35,000, or 15,000 to 30,000 Dalton.

The pharmaceutical compositions of the present application may contain a lactate-based polymer in a range of 5% to 75% by weight. The viscosity of the pharmaceutical compositions of the present application depends on the molecular weight of the polymer and biocompatible solvent used. The viscosity can range from 10,000 to 100,000 cPs. Typically, when the same solvent is used, the higher the molecular weight and the concentration of the polymer, the higher the viscosity. This can affect the degassing of the formulation, as the trapped air may be more difficult to remove from formulations with higher viscosities. Preferably the concentration of the polymer in the compositions is less than 70% by weight.

Lactate-based polymers such as poly(lactic acid) or poly(lactide) (PLA), and copolymers of lactic acid and glycolic acid (PLGA), including poly(D,L-lactide-co-glycolide) and poly(L-lactide-co-glycolide) are preferably used in the present application. The thermoplastic polyesters poly(D,L-lactide-co-glycolide) and poly(D,L-lactic acid-co-glycolic acid) can be used interchangeably and PLGA is used as an abbreviation for both. PLGA has monomer molar ratios of lactic acid to glycolic acid of between about 50:50 to about 99:1 and weight average molecular weights of between about 5,000 to about 50,000. The PLGA preferably has a monomer molar ratio of lactic acid to glycolic acid of about 50:50 (40:60 to 60:40). The PLGA further preferably has a monomer molar ratio of lactic acid to glycolic acid of about 65:35 (55:45 to 75:25). The PLGA more preferably has a monomer molar ratio of lactic acid to glycolic acid of about 75:25 (65:35 to 85:15). The PLGA further more preferably has a monomer molar ratio of lactic acid to glycolic acid of about 85:15 (75:25 to 95:5). The PLGA most preferably has a monomer molar ratio of lactic acid to glycolic acid of about 99:1. The biodegradable thermoplastic polyesters can be prepared using the methods known in the art, e.g., polycondensation and ring-opening polymerization (e.g., U.S. Pat. Nos. 4,443,340; 5,242,910; 5,310,865, which are all incorporated herein by reference). The biodegradable polymers can also be purified to remove residual monomers and oligomers using the methods known in the art, such as dissolving and re-precipitating the polymer (e.g. U.S. Pat. Nos. 4,810,775; 5,585,460, which are incorporated herein by reference). The terminal groups of the poly(DL-lactide-co-glycolide) can either be hydroxyl, carboxylic, or ester depending upon the method of polymerization and end group modification. The suitable polymers may include a monofunctional alcohol or a polyol residue. Examples of monofunctional alcohols are methanol, ethanol, or 1-dodecanol. The polyol may be a diol, triol, tetraol, pentaol and hexaol including ethylene glycol, 1,6-hexanediol, polyethylene glycol, glycerol, saccharides, glucose, sucrose, reduced saccharides such as sorbitol, and the like. Many suitable PLGAs are available commercially, and the PLGAs of specific compositions can be readily prepared according to the prior art.

The method for making such a formulation according to the present application requires weighing and mixing the materials, filtering the final product, and degassing the final product, for the formulation to be accurately filled into a single ready to use syringe. The weighing, mixing, filtering, and degassing can be performed in an isolator to control the local environment, in which the relative humidity can be set to no more than 60% at room temperature under nitrogen or argon or dry air. In a preferred embodiment of the present application, the formulation is weighed, mixed, filtered, and degassed at 15-25° C. with the humidity less than 60% and preferably less than 40% under nitrogen.

The mixing vessel can be any conventional mixer with an impeller or a planetary or double planetary mixer. The mixing of the biodegradable polymer and biocompatible solvent can be performed prior to the addition of the bioactive substance. The biocompatible solvent may be added to the mixing or compounding vessel prior to the biodegradable polymer to minimize mixing time and to prevent clumping of the polymer. If the polymer agglomerates together, it can become difficult to dissolve and would require longer mixing time to form a uniform solution. More mixing also aerates the solution more, leading to more entrapped bubbles and longer degassing times with higher expansion levels under vacuum.

In one preferred embodiment of the present application, about 90% of the biocompatible solvent is added to the mixing vessel followed by the biodegradable polymer. The biodegradable polymer can be added all at once, in a continuous manner, or in separate fractions to allow for better mixing and prevent the polymer from clumping. The biodegradable polymer can be added in equal fractions, or more preferably, by adding about 35% of the total amount of the polymer in the first step and mixing until substantially wetted, then adding the second fraction of about 30% of the total and substantially wetting, then adding the third fraction of about 25% of the total and substantially wetting, followed by adding the last fraction of about 10%. In all cases, the polymer may be substantially wetted before adding the next fraction. The polymer can be divided into up to 30 portions, preferably less than 20 portions, more preferably less than 10 portions, and most preferably less than 5 portions. The size of the polymer fractions may be such to avoid clumping of the powders which can form larger aggregates. These aggregates can increase the overall mixing and dissolution time. The polymer powder agglomerates can be broken by simple mixing or sifting before addition to the solvent. Polymer powders with larger bulk densities will take longer to dissolve. These powders can be ground further or sifted in order to aid in shortening the dissolution time.

Following dissolving the biodegradable polymer in the biocompatible solvent, the bioactive substance is added to the solution. The bioactive substance can be added all at once, or more preferably, in two or three or more, up to 20 fractions to facilitate wetting or dissolution of the bioactive substance and prevent any clumping from occurring. Like with the polymer addition, the bioactive substance may be added to the solution so that there are no agglomerates, which can increase the overall dissolution and mixing time. Agglomerates or aggregates in the powder can be broken by simple mixing or sifting before addition to the solution. The bioactive substance may be completely wetted before adding the next fraction. Once the bioactive substance has been added, the remaining fraction (about 10% to 30%) of the biocompatible solvent is added to wash any remaining powders on the compounding vessel into the formulation. Alternatively, the bioactive substance can be dissolved in about 10-30% of the total biocompatible solvent in order to more easily mix into the polymer solution. By solubilizing the bioactive substance prior to addition to the polymer solution, less bubbles will be generated from the solubilization in a less viscous solution. The final composition of the formulation is then mixed until all powders are completely solubilized. The resulting formulation is a flowable viscous liquid suspension or emulsion containing many air bubbles. This formulation must be degassed before it can be accurately filled into a ready to use syringe.

The mixing of the biodegradable polymer and bioactive substance with the biocompatible solvent can be performed in any type of mixing vessel in which the complete dissolution of the biodegradable polymer and bioactive substance can be obtained. In one embodiment of the present application, the mixing of the biodegradable polymer with the biocompatible solvent is performed in a mixing vessel with an impeller at a mixing speed from about 20 rpm to about 200 rpm. The mixing is done at such a speed to maintain the temperature in the mixing vessel at or close to ambient temperature. The total mixing time is such to ensure the complete dissolution of the polymer. The mixing time will be determined by the mixing speed, the polymer bulk density, the wetting of the powder, and the solubility of the powder in the solvent. The wetting of the polymer powder can be optimized through the addition of the powder in multiple fractions to avoid clumping. The bioactive substance is then added to the mixture and mixed at a range from about 20 rpm to about 200 rpm until complete dissolution. In another embodiment of the present application, the mixing is performed in a double planetary mixer with helical impellers and scrapers to completely dissolve the biodegradable polymer followed by the bioactive substance. In this embodiment, the helical impellers are maintained at a speed of about 20 rpm-100 rpm to maintain the temperature of the mixing vessel. Alternatively, a jacketed vessel can be used to maintain the vessel temperature at 15-25° C. if higher speeds are used.

According to the present application the filtration can occur before or after the degassing. In one preferred embodiment of the present invention, the compounding is performed in a double planetary mixer or similar vessels under vacuum. During the mixing of each fraction of the biodegradable polymer and bioactive substance, the compounding vessel of the double planetary mixer is put under relative vacuum pressure from −300 to −1000 mbar in order to remove any trapped air during the mixing and solubilization steps. This will reduce the overall degassing time needed if the formulation is mixed completely prior to degassing.

Vacuum is an air pressure measurement that is less than Earth's atmospheric pressure, about 14.7 psi or 1013 mBar. A perfect vacuum, by definition, is a space where all matter has been removed. This is an idealized description. Vacuum pressures that come close to the "almost no matter" point are difficult and expensive to create. Industrial and laboratory applications require varying degrees of vacuum that are less than perfect vacuum. This is why it is useful to understand something about units used to measure vacuum and how to convert between them. The vacuum pressure unit can be expressed in absolute and relative form as shown in the tables below (industrial Specialties Mfg. & IS MED Specialties). The relative units are used for vacuum pressures in this application.

Vacuum Pressures Unit Conversions Chart (Absolute)

| % Vacuum | ATM (standard atm) | PSIA | Torr (mm Hg) | in HG (inches Mercury) | KPa | Bar | mbar (SI unit) |
|---|---|---|---|---|---|---|---|
| 0.00 | 1.00 | 14.70 | 760.00 | 29.92 | 101.33 | 1.01 | 1013.25 |
| 1.90 | 0.98 | 14.42 | 745.56 | 29.35 | 99.40 | 0.99 | 994.00 |
| 3.30 | 0.97 | 14.21 | 734.92 | 28.93 | 97.98 | 0.98 | 979.81 |
| 6.60 | 0.93 | 13.73 | 709.84 | 27.95 | 94.64 | 0.95 | 946.38 |
| 9.80 | 0.90 | 13.26 | 685.52 | 26.99 | 91.40 | 0.91 | 913.95 |
| 10.00 | 0.90 | 13.23 | 684.00 | 26.93 | 91.19 | 0.91 | 911.93 |
| 20.00 | 0.80 | 11.76 | 608.00 | 23.94 | 81.06 | 0.81 | 810.60 |
| 30.00 | 0.70 | 10.29 | 532.00 | 20.94 | 70.93 | 0.71 | 709.28 |
| 40.00 | 0.60 | 8.82 | 456.00 | 17.95 | 60.80 | 0.61 | 607.95 |
| 50.00 | 0.50 | 7.35 | 380.00 | 14.96 | 50.66 | 0.51 | 506.63 |
| 60.00 | 0.40 | 5.88 | 304.00 | 11.97 | 40.53 | 0.41 | 405.30 |
| 65.00 | 0.35 | 5.14 | 266.00 | 10.47 | 35.46 | 0.35 | 354.64 |
| 68.00 | 0.32 | 4.70 | 243.20 | 9.57 | 32.42 | 0.32 | 324.24 |
| 70.00 | 0.30 | 4.41 | 228.00 | 8.98 | 30.40 | 0.30 | 303.98 |
| 75.00 | 0.25 | 3.67 | 190.00 | 7.48 | 25.33 | 0.25 | 253.31 |
| 80.00 | 0.20 | 2.94 | 152.00 | 5.98 | 20.27 | 0.20 | 202.65 |
| 85.00 | 0.15 | 2.20 | 114.00 | 4.49 | 15.20 | 0.15 | 151.99 |
| 87.00 | 0.13 | 1.91 | 98.80 | 3.89 | 13.17 | 0.13 | 131.72 |
| 88.00 | 0.12 | 1.76 | 91.20 | 3.59 | 12.16 | 0.12 | 121.59 |
| 89.00 | 0.11 | 1.62 | 83.60 | 3.29 | 11.15 | 0.11 | 111.46 |
| 90.00 | 0.10 | 1.47 | 76.00 | 2.99 | 10.13 | 0.10 | 101.33 |
| 92.00 | 0.08 | 1.18 | 60.80 | 2.39 | 8.11 | 0.08 | 81.06 |
| 93.00 | 0.07 | 1.03 | 53.20 | 2.09 | 7.09 | 0.07 | 70.93 |
| 95.00 | 0.05 | 0.73 | 38.00 | 1.50 | 5.07 | 0.05 | 50.66 |
| 96.60 | 0.03 | 0.50 | 25.84 | 1.02 | 3.45 | 0.03 | 34.45 |
| 97.40 | 0.03 | 0.38 | 19.76 | 0.78 | 2.63 | 0.03 | 26.34 |
| 98.70 | 0.01 | 0.19 | 9.88 | 0.39 | 1.32 | 0.01 | 13.17 |
| 100.00 | 0.00 | 0.00 | 0.00 | 0.00 | 0.00 | 0.00 | 0.00 |

Vacuum Pressures Unit Conversions Chart (Relative)

| % Vacuum | ATM (standard atmosphere) | PSIG negative gauge | Torr (mm Hg) negative gauge | inches Hg negative gauge | kPa negative gauge | bar negative gauge | mbar negative gauge |
|---|---|---|---|---|---|---|---|
| 1.4 | 0.99 | −0.21 | −10.64 | −0.42 | −1.42 | −0.01 | −14.19 |
| 3.3 | 0.97 | −0.48 | −25.08 | −0.99 | −3.34 | −0.03 | −33.44 |
| 6.6 | 0.93 | −0.97 | −50.16 | −1.97 | −6.69 | −0.07 | −66.87 |
| 7.9 | 0.92 | −1.16 | −60.04 | −2.36 | −8 | −0.08 | −80.05 |
| 9.8 | 0.9 | −1.44 | −74.48 | −2.93 | −9.93 | −0.1 | −99.3 |
| 10 | 0.9 | −1.47 | −76 | −2.99 | −10.13 | −0.1 | −101.33 |
| 20 | 0.8 | −2.94 | −152 | −5.98 | −20.27 | −0.2 | −202.65 |
| 25 | 0.75 | −3.67 | −190 | −7.48 | −25.33 | −0.25 | −253.31 |
| 30 | 0.7 | −4.41 | −228 | −8.98 | −30.4 | −0.3 | −303.98 |
| 33 | 0.67 | −4.85 | −250.8 | −9.87 | −33.44 | −0.33 | −334.37 |
| 35 | 0.65 | −5.14 | −266 | −10.47 | −35.46 | −0.35 | −354.64 |
| 40 | 0.6 | −5.88 | −304 | −11.97 | −40.53 | −0.41 | −405.3 |
| 45 | 0.55 | −6.61 | −342 | −13.46 | −45.6 | −0.46 | −455.96 |
| 50 | 0.5 | −7.35 | −380 | −14.96 | −50.66 | −0.51 | −506.63 |
| 55 | 0.45 | −8.08 | −418 | −16.46 | −55.73 | −0.56 | −557.29 |
| 60 | 0.4 | −8.82 | −456 | −17.95 | −60.8 | −0.61 | −607.95 |

-continued

| % Vacuum | ATM (standard atmosphere) | PSIG negative gauge | Torr (mm Hg) negative gauge | inches Hg negative gauge | kPa negative gauge | bar negative gauge | mbar negative gauge |
|---|---|---|---|---|---|---|---|
| 61 | 0.39 | −8.96 | −463.6 | −18.25 | −61.81 | −0.62 | −618.08 |
| 65 | 0.35 | −9.55 | −494 | −19.45 | −65.86 | −0.66 | −658.61 |
| 68 | 0.32 | −9.99 | −516.8 | −20.35 | −68.9 | −0.69 | −689.01 |
| 70 | 0.3 | −10.29 | −532 | −20.94 | −70.93 | −0.71 | −709.28 |
| 75 | 0.25 | −11.02 | −570 | −22.44 | −75.99 | −0.76 | −759.94 |
| 80 | 0.2 | −11.76 | −608 | −23.94 | −81.06 | −0.81 | −810.6 |
| 85 | 0.15 | −12.49 | −646 | −25.43 | −86.13 | −0.86 | −861.26 |
| 87 | 0.13 | −12.79 | −661.2 | −26.03 | −88.15 | −0.88 | −881.53 |
| 88 | 0.12 | −12.93 | −668.8 | −26.33 | −89.17 | −0.89 | −891.66 |
| 89 | 0.11 | −13.08 | −676.4 | −26.63 | −90.18 | −0.9 | −901.79 |
| 90 | 0.1 | −13.23 | −684 | −26.93 | −91.19 | −0.91 | −911.93 |
| 92 | 0.08 | −13.52 | −699.2 | −27.53 | −93.22 | −0.93 | −932.19 |
| 93 | 0.07 | −13.67 | −706.8 | −27.83 | −94.23 | −0.94 | −942.32 |
| 95 | 0.05 | −13.96 | −722 | −28.43 | −96.26 | −0.96 | −962.59 |
| 96.6 | 0.03 | −14.2 | −734.16 | −28.9 | −97.88 | −0.98 | −978.8 |
| 97.4 | 0.03 | −14.31 | −740.24 | −29.14 | −98.69 | −0.99 | −986.91 |
| 98.70 | 0.01 | −14.50 | −750.12 | −29.53 | −100.01 | −1.00 | −1000.08 |
| 100 | 0 | −14.7 | −760 | −29.92 | −101.33 | −1.01 | −1013.25 |

The formulation of the present application is a viscous liquid suspension or emulsion. In certain embodiments, the biodegradable polymer is dissolved in biocompatible solvent with high solubility (polymer rich phase) and the bioactive substance is dissolved in biocompatible solvent with high solubility (bioactive substance rich phase). It was unexpectedly found that the polymer rich phase is not miscible with the bioactive substance rich phase. When the polymer rich phase is mixed with the bioactive substance rich phase, the resulting formulation is not a homogenous solution, but rather a suspension or emulsion in which the bioactive substance rich liquid droplets are suspended in the continuous polymer solution phase. In another embodiment, the biodegradable polymer is dissolved in the biocompatible solvent first and then the bioactive substance powder is added and mixed to dissolve. Again, the resulting formulation is characterized as a suspension or emulsion as the bioactive substance rich liquid droplets are suspended in the continuous polymer solution phase.

In one preferred embodiment of the present invention, leuprolide mesylate is mixed with a PLA polymer solution in NMP. The formulation manufactured by the present application is a milky opaque viscous flowable composition characterized as leuprolide-rich phase droplets suspended in a PLA-rich continuous phase having a viscosity greater than 10,000 centipoise (cPs). The viscosity can range from 10,000 to 100,000 cPs depending on the final compositions.

In another preferred embodiment of the present invention, leuprolide mesylate is mixed with a PLGA polymer solution in NMP. The formulation manufactured by the present application is a milky opaque viscous flowable composition characterized as leuprolide-rich phase droplets suspended in a PLGA-rich continuous phase.

In still another preferred embodiment of the present invention, triptorelin mesylate is mixed with a PLA or PLGA polymer solution in NMP. The formulation manufactured by the present application is a milky opaque viscous flowable composition characterized as triptorelin-rich phase droplets suspended in a polymer-rich continuous phase having a viscosity greater than 10,000 centipoise (cPs). The viscosity can range from 10,000 to 100,000 cPs depending on the final compositions.

The sizes of these droplets can vary depending on the mixing method. The uniformity of the formulation will depend on the size and size distribution of these droplets. In order to manufacture a formulation with a more uniform distribution of leuprolide-rich or triptorelin-rich droplets, a stainless steel mesh, or filter, is used to remove any particulate matters such as foreign particles or polymer agglomerates from the formulation as well as to control or narrow the distribution of droplet sizes in the formulation. The pore size ranges from about 5 μm to about 150 μm, preferably from about 10 μm to about 100 μm, more preferably from about 20 μm to about 80 μm, most preferably from about 40 μm to about 60 μm.

Due to the high viscosity of the formulation, it is necessary to apply upstream pressure to push the formulation through the filter. In a preferred embodiment of the present invention, in addition to the inlet pressure, a vacuum is pulled downstream to aid the movement of the formulation through the filter. Preferably, the inlet pressure is 1 bar to 10 bar and the outlet vacuum (relative) is about −300 mbar to −1000 mbar. In another preferred embodiment of the present invention, the leuprolide formulation leaves the compounding vessel under a pressure of 1 to 3 bar and is filtered through a 40 μm stainless steel mesh to remove particulate matters, such as any foreign particles or polymer agglomerates, from the formulation and to narrow the leuprolide-rich particle size distribution. A downstream vacuum pressure (relative) of −300 mbar to −1000 mbar is also used to help pull the formulation through the filter. In addition, the vacuum can also help to degas the formulation in the receiving vessel. The stronger the vacuum used, the more bubbles can be removed from the formulation in the receiving vessel prior to the degassing method. This can reduce the overall degassing time. In one preferred embodiment of the present invention, the receiving vessel vacuum (relative) is set to about −700, −750, −800, −850, −900, −950, or −980 mbar to degas the formulation as it is filtered, reducing the overall needed degassing time.

The method of the present application also describes a degassing procedure for the formulation. In addition to the mixing method of the current application, the solubilization of the polymer and bioactive substance traps gas or bubbles into the formulation. The formulation cannot be accurately filled into syringes due to the presence of such a significant amount of trapped bubbles in this highly viscous formulation. The bubbles can be compressed under pressure and can expand when the pressure is released. This can cause variability in the fill weight accuracy. Therefore, the formulation requires degassing prior to filling. According to the present application, the formulation can be degassed before or after the filtration step. Due to the high viscosity of such a formulation of the present application, a vacuum is required to remove the gas in a reasonable time. The degassing time will depend on the final vacuum pressure that can be obtained. The higher the vacuum pressure, the shorter the total degassing time. However, pulling too high a vacuum pressure can lead to the trapped gas coming out too rapidly and causing the formulation to froth up in the degassing vessel and overflow the degassing vessel. Pulling a higher vacuum can also lead to the solvent evaporation depending on the vapor pressure of the solvent. This loss of solvent would change the overall formulation composition.

When the vacuum pressure (relative) is set to about –900 mbar, the formulation will expand and rise in the degassing vessel. By holding at this vacuum pressure, bubbles will begin to move up through the formulation and coalesce and pop at the surface. In order to decrease the total degassing time, the vacuum pressure can be increased after a certain time at about –900 mbar. While the polymer solution could be easily degassed by increasing the vacuum pressure (relative) from –900 mbar to –950 mbar, it was unexpectedly found that when the vacuum pressure was changed from –900 mbar to –950 mbar, the formulation, due to higher viscosity, rose to a much higher level in the degassing vessel than for just the polymer solution without bioactive substance.

While degassing in a vessel that was ⅓ filled with a formulation containing 13% leuprolide mesylate with a polymer solution of 57.5% PLA in NMP, where the polymer had a molecular weight of about 16,000 dalton, the vacuum pressure (relative) could be adjusted stepwise from about –900 mbar to about –950 mbar and the formulation degassed without overflowing the degassing vessel. It was unexpectedly found that when using a degassing vessel that was ⅓ filled with a formulation with 8% leuprolide mesylate and a polymer solution of 57.7% PLGA in NMP, where the polymer had a molecular weight of about 19,800 dalton, the formulation overflowed the vacuum vessel when the vacuum pressure was changed from –900 mbar to –950 mbar. The type of polymer and molecular weight have significant impact on the selection of degassing parameters to perform degassing properly.

In a preferred embodiment of the present invention, the fill level in the degassing vessel may be from 10-50% to allow for the formulation to rise as the pressure is dropped and the bubbles come out. More preferably, the fill level of the degassing vessel may be from 15-35% to allow sufficient room for the formulation expansion upon degassing. It is not advantageous to just use a larger degassing vessel, as not only will this take up more space, but a larger vessel will have more loss of formulation on the walls of the vessel and increase the manufacturing costs. The design of the degassing vessel also is important. Using a narrower vessel would result in the product filling the degassing vessel to a higher level, increasing the distance the bubbles need to travel to degas the product. The larger the diameter of the degassing vessel, the lower the level of product in the degassing vessel, which reduces the distance the bubbles need to travel in the product bulk and would reduce the overall degassing time. The suitable degassing vessel may have a ratio of degassing vessel height to degassing vessel diameter from 10:1 to 1:1, preferably 5:1 to 1:1.

In one preferred embodiment of the present invention for degassing a leuprolide formulation containing a PLGA polymer with a molecular weight of about 19,800 dalton, a degassing vessel is filled to a level of approximately 33% of the total volume. It was unexpectedly found that by releasing the vacuum followed by applying the same vacuum pressure, the expansion level of the formulation was lower than where it started. Therefore, the degassing method is performed stepwise to avoid overflow of the formulation from the vessel and allow for increasing the vacuum pressure to decrease the total degassing time. The initial vacuum pressure is set to about –900 mbar. After holding for one hour, the vacuum is released and a new vacuum pressure set to about –920 mbar and the formulation will rise to approximately the same level as it was previously. This pressure is held for one hour and then released. A new vacuum pressure is set to about –930 mbar. This method can be repeated to get to the final vacuum pressure without any overflow of the product. The venting of the vacuum results in some of the larger bubbles collapsing and popping. The next time the vacuum is pulled to the same pressure, it will be lower since there will be fewer bubbles. The final pressure may be significantly lower than the vapor pressure of the biocompatible solvent to prevent any loss of material, changing the composition of the final formulation. The total degassing time can thus be shortened by increasing the vacuum pressure, and overflow and loss can be prevented by increasing the vacuum pressure in a stepwise manner. The degassed formulation can then be accurately filled into ready to use syringes.

It was also unexpectedly found that when degassing in larger intervals (3×11-hour vacuum intervals), inhomogeneous bulk product was surprisingly obtained. A gradient was sometimes found after long degassing times, with a higher bioactive substance concentration at the bottom of the degassing vessel and a lower one towards the top of the degassing vessel but below the top surface layer. The concentration in the top surface layer is as high as or higher than that in the bottom. The degassing causes the product to expand, which reduces the overall viscosity of the product. Having the product at a lower viscosity for longer times can result in the bioactive substance rich droplets migration down the filling vessel. Using shorter, more frequent degassing/venting cycles will reduce the overall expansion of the formulation and also reduce the time the formulation is expanded. This will lead to keeping the product viscosity higher, preventing any inhomogeneity from occurring. Thus, it is preferable to degas in multiple shorter vacuum/venting cycles.

In certain embodiment, the degassing is performed after all compounding mixing steps and filtration step, if any. The degassing step is performed by four (4) or more vacuum/vent cycles of applying a relative vacuum pressure between –300 mbar and –1000 mbar to the compounding vessel or a degassing vessel containing the formulation prepared, maintaining the vacuum for a time period between 5 min and 720 min, and releasing the vacuum to allow venting; wherein the vacuum level maintained at each vacuum/vent cycle is at least as strong as or stronger than that maintained in an immediately previous cycle. The vacuum target for the first vacuum/vent cycle is set at –300, –400, –500, –600, –700, –800, or –900 mbar depending on the viscosity of the formulation and the potential expansion level under a known vacuum. The vacuum level maintained at each subsequent vacuum/vent cycle is at least as strong as or stronger than that maintained in an immediately previous cycle. The vacuum level maintained at the last or final vacuum/vent cycle is preferably at –950 mbar or stronger.

In another embodiment, the degassing is performed during compounding step at each material introduction/mixing step. About 90% of the total amount of a biocompatible solvent is introduced into the compounding vessel. The biodegradable polymer is divided into 2 or more fractions. The first fraction of the biodegradable polymer is added in the compounding vessel containing the biocompatible solvent. A target vacuum between −300 and −1000 mbar including −300, −400, −500, −600, −700, −800, or −900 mbar depending on the molecular weight of the biodegradable polymer is applied to the compounding vessel before or during mixing. After mixing for 5 minutes to 2 hours or until the biodegradable polymer is wetted or substantially dissolved, the vacuum is released to vent. Then each subsequent fraction of the biodegradable polymer or LHRH agonist is separately and sequentially introduced into the compounding vessel after the biodegradable polymer or LHRH agonist previously added in the compounding vessel is wetted or substantially dissolved. A target vacuum between −300 and −1000 mbar including −300, −400, −500, −600, −700, −800, or −900 mbar depending on the molecular weight of the biodegradable polymer is applied to the compounding vessel before or during mixing. After mixing for 5 minutes to 2 hours or until the biodegradable polymer is wetted or substantially dissolved, the vacuum is released to vent. The material introduction/vacuum/mixing/venting is repeated until all the biodegradable polymer and LHRH agonist are added and substantially dissolved to form a substantially bubble free and homogeneous formulation. The vacuum level maintained at each subsequent vacuum/vent cycle is at least as strong as or stronger than that maintained in an immediately previous cycle. The vacuum level maintained at the last or final vacuum/vent cycle is preferably at −950 mbar or stronger.

The product does not need to be completely degassed to enable accurate filling into syringes. The bulk product needs to be degassed substantially enough to prevent the expansion of these bubbles after they are pushed out of the filling nozzle into a syringe. Due to the high viscosity of the product, at least 1.0 bar of pressure needs to be applied to the filling tank to push the product into the pump to fill into syringes. The drop in pressure from the filling nozzle to the syringe at ambient pressure can result in product expansion if there are too many bubbles present. Thus, in a preferred embodiment of the present invention, the bulk product may be almost free of bubbles where there can still be some remaining bubbles visible on the surface of the product in the vessel.

In a preferred embodiment of the present invention, a method is provided for making injectable compositions for controlled release drug delivery by forming economical, practical, and efficient controlled release delivery systems that comprise a) a bioactive substance or salt thereof; b) a biocompatible solvent; and c) a biodegradable polymer. The method involves mixing the raw materials, followed by filtering and degassing the product, where the mixing, filtering, and degassing are performed under controlled humidity of less than 60%, preferably less than 40% at 15-25° C. under a nitrogen atmosphere, the filtration is performed through a 40 μm stainless steel mesh with an inlet pressure of 1-2 bar and an outlet relative vacuum of −0.8 to −1.0 bar, and the degassing is performed under a relative vacuum from −300 mbar to −1000 mbar where the initial vacuum pressure is at the lower end and increased step wise or gradually to the final vacuum pressure, preventing product overflow and concentration gradient formation and still completing in a reasonable period of time. The resulting formulation is a uniform liquid suspension or emulsion of bioactive substance rich droplets suspended in a polymer rich continuous phase with minimal to no trapped bubbles.

In another preferred embodiment of the present invention, a method is provided for making an injectable composition for controlled release drug delivery of leuprolide comprising: mixing the raw materials, filtering the product, and degassing the product where these steps are performed under controlled humidity of less than 40% at 15-25° C. under a nitrogen, or argon, or dried air atmosphere, the filtration is performed through a 40 μm stainless steel mesh with an inlet pressure of 1 to 10 bar and an outlet relative vacuum of −300 to −1000 mbar before or after degassing step, and the degassing is performed stepwise under a relative vacuum from −300 mbar to −1000 mbar, where the degassing cycle times are no more than 5 hours continuously before venting and resetting the vacuum. The formulation can then be optionally mixed by slow rotational or mechanical mixing to ensure homogeneity.

In still another preferred embodiment of the present invention, a method is provided for making an injectable composition for controlled release drug delivery of leuprolide comprising: adding the raw materials in a double planetary mixer or similar mixer, followed by degassing in the same vessel while mixing. The degassing is performed stepwise under a relative vacuum of −300 mbar to −980 mbar. The filtration is then performed through a 40 μm stainless steel mesh with an inlet pressure of 1 to 2 bar and an outlet relative vacuum of −0.8 to −1.0 bar. The resulting formulation is a uniform liquid suspension of leuprolide rich droplets suspended in a polymer rich continuous phase with minimal to no trapped bubbles. Preferably, the composition is easily injectable and can be packaged into a kit comprising a step to accurately fill the composition into a syringe in a ready-to-use configuration.

In one further preferred embodiment of the present invention, about 50%-90% of the biocompatible solvent is added to the mixing vessel followed by the biodegradable polymer. The biodegradable polymer can be added all at once, in a continuous manner, or in separate fractions to allow for better mixing and prevent the polymer from clumping. After each addition of the polymer, the mixing vessel is closed and a vacuum is applied during mixing. This will allow removal of any trapped air and prevent aeration during mixing. The biodegradable polymer can be added in equal or variable fractions. After first fraction is added, the mixing vessel is closed, a vacuum is applied, and mixing performed until the biodegradable polymer is substantially wetted, the mixing is stopped and vacuum is released, then the second fraction is added, the mixing vessel is closed, a vacuum is applied, and mixing performed until the added fraction is substantially wetted, the mixing is stopped and vacuum is released, and continued to the next step. The process is repeated until all fractions of polymer are added into the mixing vessel and dissolved. The polymer can be divided into up to 30 portions or more. The size of the polymer fractions may be such to avoid clumping of the powders which can form larger agglomerates. These agglomerates can increase the overall mixing and dissolution time. The polymer powder agglomerates can be broken by simple mixing or sifting before addition to the solvent. Polymer powders with larger bulk densities will take longer to dissolve. These powders can be ground further or sifted in order to aid in shortening the dissolution time.

In one further preferred embodiment of the present invention, the biodegradable polymer can be added via a material introduction port in a continuous manner during mixing to allow for better mixing and prevent the polymer from clumping. The mixing and polymer introduction are carried out under vacuum.

Following dissolving the biodegradable polymer in the biocompatible solvent, the bioactive substance is added to the solution. The bioactive substance can be added all at once, or more preferably, in two or three or more, up to 20 fractions to facilitate wetting or dissolution of the bioactive substance and to prevent any clumping from occurring. Like with the polymer addition, the bioactive substance may be added to the solution so that there are no agglomerates, which can increase the overall dissolution and mixing time. After each fraction is added, the mixing vessel is closed, a vacuum is applied, and the fraction mixed until substantially wetted or dissolved, the mixing is stopped and vacuum is released, then continue to the next step until all the bioactive substance is added. Agglomerates or aggregates in the powder can be broken by simple mixing or sifting before addition to the solution. The bioactive substance may be substantially wetted before adding the next fraction. Once the bioactive substance has been added, the remaining fraction (about 10% to 30%) of the biocompatible solvent is added to wash any remaining powders on the compounding vessel into the formulation. Alternatively, the bioactive substance can be dissolved in about 10-30% of the total biocompatible solvent in order to more easily mix into the polymer solution. By solubilizing the bioactive substance prior to addition to the polymer solution, fewer bubbles will be generated from the solubilization in a less viscous solution. The final composition of the formulation is then mixed under vacuum until all powders are completely solubilized and the majority of bubbles are removed. The resulting formulation is a flowable viscous liquid suspension or emulsion containing few air bubbles.

Alternatively, in another further preferred embodiment of the present invention, about 70%-90% of the biocompatible solvent is added to the mixing vessel followed by the biodegradable polymer. The biodegradable polymer can be added all at once, in a continuous manner, or in separate fractions to allow for better mixing and prevent the polymer from clumping. The biodegradable polymer can be added in equal or variable fractions. After the first fraction is added, start mixing until the polymer is substantially wetted or dissolved, then add the second fraction, and mix until substantially wetted or dissolved, then continue to the next step. The process is repeated until all fractions of polymer are added and dissolved. The polymer can be divided into up to 30 portions. The size of the polymer fractions may be such to avoid clumping of the powders which can form larger agglomerates. These agglomerates can increase the overall mixing and dissolution time. The polymer powder agglomerates can be broken by simple mixing or sifting before addition to the solvent. Polymer powders with larger bulk densities will take longer to dissolve. These powders can be ground further or sifted in order to aid in shortening the dissolution time.

In a further preferred embodiment of the present application about 70%-90% of the biocompatible solvent is added to the mixing vessel followed by the biodegradable polymer. The biodegradable polymer can be added all at once, in a continuous manner, or in separate fractions to allow for better mixing and prevent the polymer from clumping. The biodegradable polymer can be added in equal or variable fractions. After first fraction is added, start mixing at a lower mixing speed (20 rpm) to limit the air incorporation into the mixture until the polymer is substantially wetted or dissolved, then turn on the vacuum at the lower end of the range (−300 mbar) to prevent product overflow and increase the mixing speed (60-90 rpm). The vacuum level can then be increased step wise to the higher end of the range (−1000 mbar) to degas the solution. The process is repeated until all fractions of polymer and bioactive substance are added and dissolved. It is surprisingly discovered that the final formulation obtained is substantially bubble free and homogeneous. This process resolved the formulation gradient or inhomogeneous problem.

Following dissolving the biodegradable polymer in the biocompatible solvent, the bioactive substance is added to the solution. The bioactive substance can be added all at once, or more preferably, in two or three or more up to 20 fractions to facilitate wetting or dissolution of the bioactive substance and prevent any clumping from occurring. Like with the polymer addition, the bioactive substance may be added to the solution so that there are no agglomerates. After each fraction is added, mix until the polymer is substantially wetted or dissolved, and then continue to the next step until all bioactive substance is added and dissolved. Agglomerates or aggregates in the powder can be broken by simple mixing or sifting before addition to the solution. The bioactive substance may be substantially wetted before adding the next fraction. Once the bioactive substance has been added, the remaining fraction (about 10% to 30%) of the biocompatible solvent is added to wash any remaining powders on the compounding vessel into the formulation. Alternatively, the bioactive substance can be dissolved in about 10-30% of the total biocompatible solvent in order to more easily mix into the polymer solution. By solubilizing the bioactive substance prior to addition to the polymer solution, fewer bubbles will be generated from the solubilization in a less viscous solution. The final composition of the formulation is then mixed under vacuum until all powders are completely solubilized and majority of bubbles are removed. The resulting formulation is a flowable viscous liquid suspension or emulsion containing few air bubbles.

The formulations obtained above can be further filtered. The filtration is performed through a 40 µm stainless steel mesh with an inlet pressure of 1 to 10 bar and an outlet relative vacuum of −300 to −1000 mbar. The resulting formulation is a uniform liquid suspension or emulsion of bioactive substance rich droplets suspended in a polymer rich continuous phase with minimal to no trapped bubbles. Preferably, the composition is easily injectable and can be packaged into a kit comprising a step to accurately fill the composition into a syringe in a ready-to-use configuration.

The composition in the kit is stable for a reasonable period of time, preferably at least two years, to have a suitable storage shelf-life under controlled storage conditions. The composition is preferably injected into a subject to form in situ an implant, from which the bioactive substance is released in a therapeutic effective amount over a desired, extended period of time.

EXAMPLES

The following examples illustrate the compositions of the present application. The examples do not limit the invention, but are provided to teach how to make useful controlled release drug delivery compositions.

Example 1: Manufacture of a Viscous Polymer Solution

In a mixing vessel under nitrogen, at a temperature between 15 and 25° C. and at a relative humidity below 60%, 749 g of NMP was added, followed by the addition of a PLA polymer (Resomer R 202 S, IV 0.22, Evonik lot #R120600501) using a double marine-style impeller at a speed of 100 rpm. The polymer was divided and added in sixteen (16) fractions to aid in the wetting of the polymer powder and to prevent clumping. The first fifteen (15) fractions were all roughly the same amounts of about 100 g. The last fraction added less than 100 g so that the total polymer addition was 1508.5 g and resulted in a 68% polymer solution in NMP. Each polymer fraction addition time ranged from about 5 to 40 minutes to ensure the powder was substantially wetted before adding the next aliquot. A large amount of trapped bubbles caused the polymer solution to appear opaque and difficult to judge if the full dissolution of the polymer in NMP was achieved. The dissolution was continued overnight to ensure complete dissolution of the polymer.

The solution was then fed through a 40 μm stainless steel mesh to filter off any particulate matters or polymer agglomerates from the solution. A pressure of approximately 8 bar was used to push the solution through the mesh, while a downstream relative vacuum of approximately –1000 mbar was pulled to help pull the solution through the filter. It took approximately 30 minutes to pass the material from the mixing vessel through the filter to the receiving vessel. After filtration, the filter was examined and no polymer aggregates were observed, indicating the polymer was completely dissolved.

Once in the degassing vessel, an initial vacuum of about –1000 mbar was applied and the polymer solution began to froth due to the large amount of trapped air and high viscosity of the product. Decreasing the vacuum level to about –300 mbar reduced the frothing and prevented any overflow of the solution. After about 2.5 hours the vacuum level was gradually increased to about –1000 mbar and the solution left under vacuum for no more than 5 days to fully degas the solution.

The solution was then filled into 1 mL long syringes using rotary piston pumps (SV 122V, Optima) with a pressure of about 6 bar on the filling tank to aid in priming the pump. With a pump speed rotation of 2%, dose setting of 0.32 mL and back absorption of 1.00 mm, a fill weight of 370 mg±20 mg was achieved.

Example 2: Filtering Viscous Formulation

A stainless steel filter with pore sizes of about 25 μm was used to filter a formulation containing 13.5% leuprolide mesylate in a 57.5% PLA (Evonik Resomer R 202 S, IV 0.22) in NMP solution. An inlet pressure of 2 bars was used and an outlet relative vacuum of –800 mbar was used. The formulation was recovered and analyzed for leuprolide-rich phase droplet sizes after the filtration. FIG. 1 shows a representative image of the droplets in the formulation using an inverted confocal microscope. The droplets were all less than about 25 μm. A fairly uniform distribution of droplets could be attained using this method.

Example 3: Manufacture of Formulation Containing Leuprolide and PLA

A PLA polymer formulation containing leuprolide was prepared using the following method. The final formulation was about 13.5% leuprolide mesylate in about 57.5% PLA (Evonik Resomer R 202 S, IV 0.22) in NMP solution. The mixing, filtration, and degassing all took place under nitrogen and a temperature of 15-25° C. at <40% relative humidity. The PLA had a molecular weight of approximately 16,500 dalton. The polymer solution was prepared similar to the method as described in the Example 1 with a slight modification to divide the polymer into four fractions instead of sixteen. About 330 g of the NMP was added to a mixing vessel followed by about 190.0 g PLA polymer. The solution was mixed until all the polymer was substantially wetted or dissolved. Then about 124.3 g PLA was added and solution mixed again until all the polymer was substantially wetted or dissolved. Then about 124.0 g PLA was added and solution mixed again until all the polymer was substantially wetted or dissolved. Finally, about 50 g remaining PLA was added and the solution was mixed until a homogenous solution was obtained. Then 68.0 g leuprolide mesylate was added to the solution and mixed until all leuprolide mesylate was substantially wetted or dissolved. Then 67.5 g leuprolide mesylate was added and the content was mixed until all leuprolide mesylate was substantially wetted or dissolved. Finally, 37.4 g NMP was used to wash down any materials on the side wall of the mixing vessel and the formulation was mixed until a homogenous suspension or emulsion was obtained.

The resulting formulation was then fed through a 40 μm stainless steel filter using an upstream pressure of 2 bar and a downstream vacuum pressure of –0.8 bar. The formulation was filtered into a degassing (receiving) vessel. The filtrate volume was about ⅓ of the total volume capacity of vessel. The formulation was then degassed using an initial vacuum pressure of –900 mbar. After about 12 hours, the vacuum pressure was set to –950 mbar. The formulation was unexpectedly found to overflow the degassing vessel and into the vacuum lines. This indicates that the volume of the formulation is more than tripled under the vacuum of –950 mbar. The vacuum was released to vent to the atmosphere. Then the vacuum was applied again and increased stepwise such as the vacuum pressure was increased and set to –910 mbar for 2 hours, and the vacuum was released back to the atmosphere. Then the vacuum pressure was increased and set to –930 mbar for 2 hours, and again the vacuum was released back to the atmosphere. Then the vacuum pressure was increased and set to –940 mbar for 2 hours, and again the vacuum was released back to the atmosphere. Then the vacuum pressure was increased and set to –950 mbar for 12 hours and the vacuum was released back to the atmosphere. The resulting formulation was substantially bubble free.

Example 4: Manufacture of Formulation Containing Leuprolide

A polymer formulation containing leuprolide was prepared using the following method. The final formulation was 8% leuprolide mesylate in a 58% PLGA (8515 PLGA, Durect lot #A16-088, IV-0.24) in NMP solution. The mixing, filtration, and degassing all took place in an isolator under nitrogen and a temperature of 15-25° C. at <40% relative humidity. The PLGA had a molecular weight of approximately 19,800 dalton and a monomer lactic acid to glycolic acid ratio of about 85:15 or between 80:20 and 90:10. The polymer solution was prepared similar to the method as described in the Example 3 with a slight modification to divide the polymer into 4 fractions. About 90% of the NMP was added to a mixing vessel followed by about 40% of the PLGA polymer. The solution was mixed until all the polymer was substantially wetted or dissolved. Then about 25% of the PLGA was added and solution mixed again until all the polymer was substantially wetted or dissolved. Then about 25% of the PLGA was added and solution mixed again until all polymer was substantially wetted or dissolved. Finally, all the remaining PLGA, about 10%, was added, and the solution was mixed until a homogenous solution was obtained. Then about 50% of the leuprolide mesylate was added to the solution and mixed until all leuprolide mesylate was substantially wetted or dissolved. Then the remaining leuprolide mesylate fraction was added and the content was mixed until all leuprolide mesylate was substantially wetted or dissolved. Next, the remaining about 10% of NMP was used to wash down any materials on the side wall of the mixing vessel. Finally, the formulation was further mixed for at least 15 minutes until a homogenous suspension or emulsion was obtained.

The resulting formulation was then fed through a 40 μm stainless steel filter using an upstream pressure of 2 bar and a downstream vacuum pressure of −0.8 bar into a degassing (receiving) vessel. The formulation occupied approximately ⅓ of the total volume capacity of the receiving degassing vessel. The formulation was then degassed using an initial pressure of −900 mbar. After a specified period of time the vacuum pressure was set to −950 mbar. The formulation was unexpectedly found to overflow the degassing vessel and into the vacuum lines.

Figure 2:
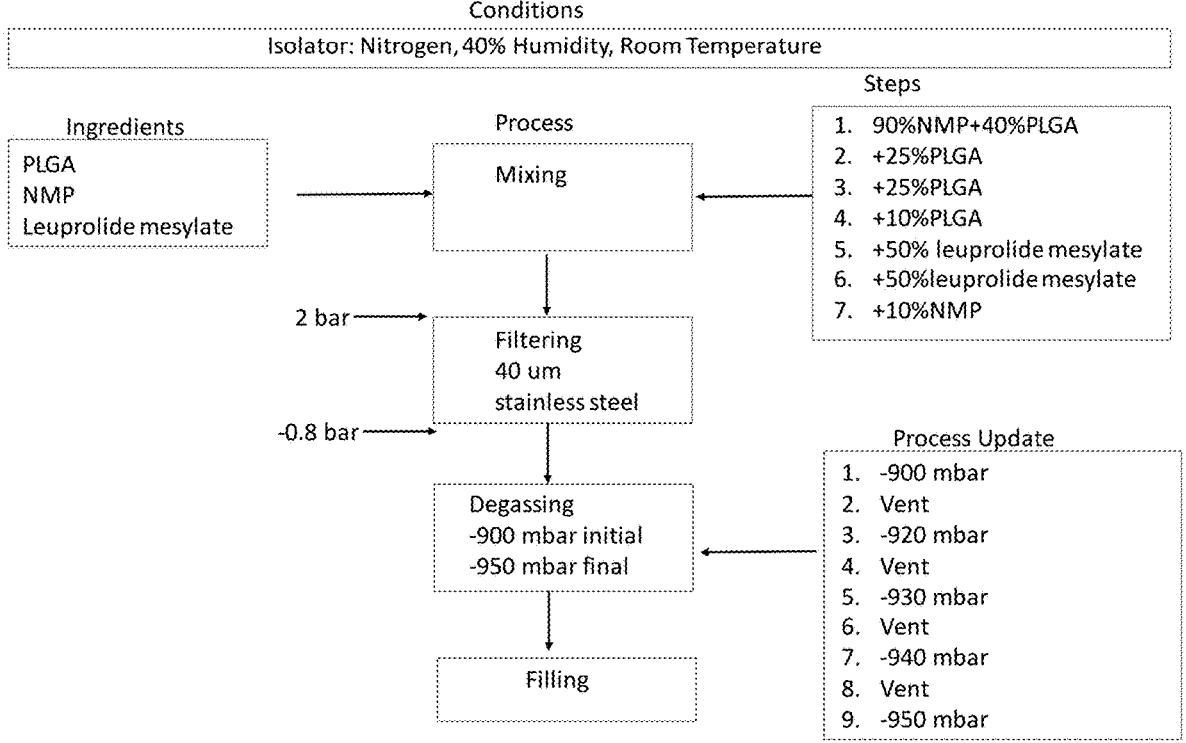
FIG. 2 shows a flowchart of the manufacturing method based on an embodiment of the present invention.

A change in the degassing method is necessary to degas the formulation without overflow as shown in FIG. 2. In this experiment, the vacuum pressure was set at −900 mbar and held for 1 hour. Then the vacuum was released to vent and allow some bubbles to burst. The vacuum was reset to −920 mbar and again held for 1 hour. The pressure was then released to vent and allow some bubbles to burst. The vacuum was then reset to −930 mbar and held for 1 hour. The pressure was then released to vent and allow some bubbles to burst. The vacuum was then reset to −940 mbar and held for 1 hour. The vacuum was then released to vent and allow some bubbles to burst. The vacuum was then reset to −950 mbar. The bubble level again rose, but did not overflow. In this way, the formulation can be degassed at a pressure of −950 mbar without any overflow similar to the example 3. This procedure can be repeated, progressively increasing the vacuum pressure between each cycle if needed.

Example 5: Degassing of a Formulation Containing Leuprolide and PLGA

Figure 3:
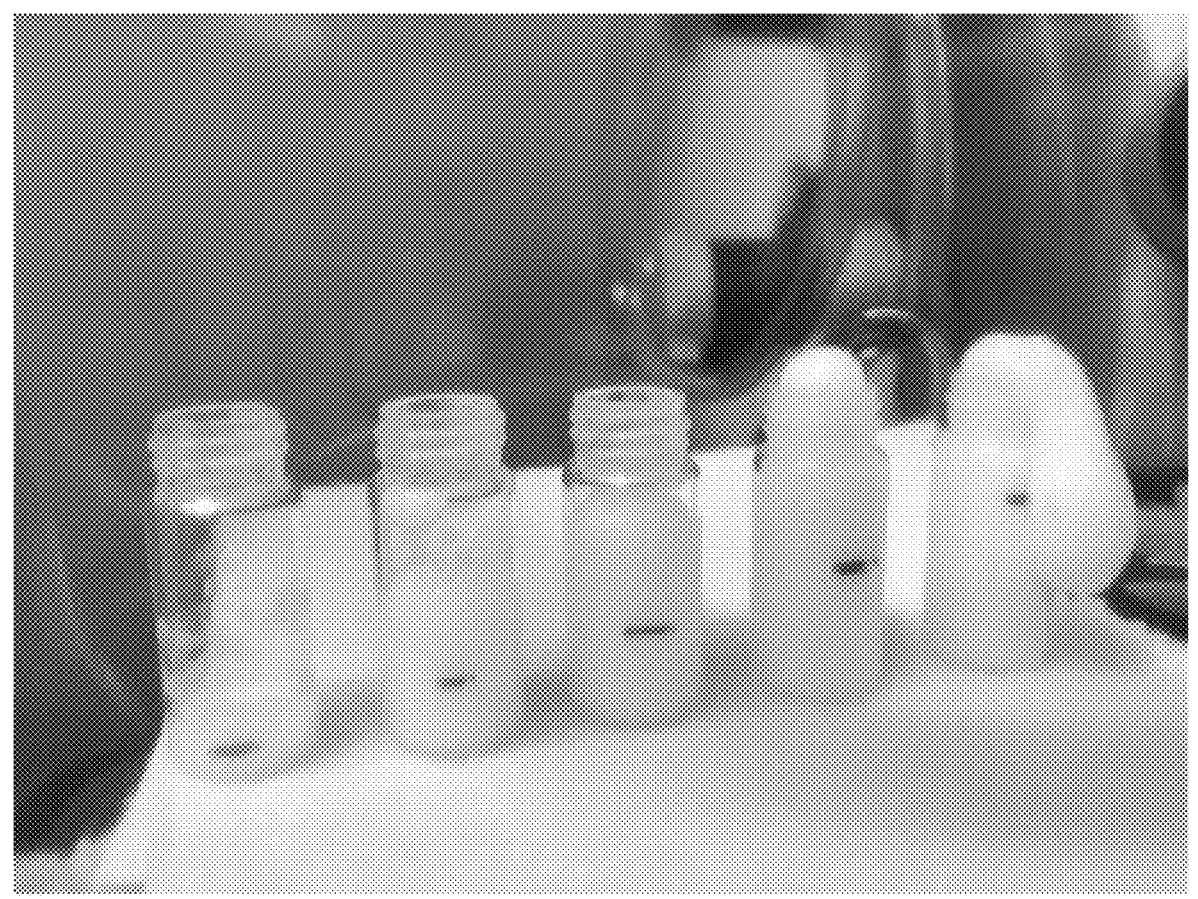
FIG. 3 shows a formulation of 8% leuprolide mesylate in 58% PLGA/NMP (IV=0.24, MW=19 k) after reaching a vacuum pressure of −950 mbar going directly from −900 mbar in accordance with an embodiment of the present invention. The black lines on the vials indicated the initial fill levels, which were 10%, 25%, 33%, 50%, and 67% from left to right, respectively.

A formulation containing 8% leuprolide mesylate was prepared in a 58% PLGA in NMP solution. The PLGA had a molecular weight of approximately 19,800 dalton (an inherent viscosity of 0.24) and a monomer lactic acid to glycolic acid ratio of about 85:15 (80:20-90:10). The formulation was to be degassed. The formulation was added to different 4 mL vials and filled to 10%, 25%, 33%, 50%, and 67% of the volume of each vial. The vacuum pressure was then set to −900 mbar. The volume of the formulations increased slightly as the bubbles in the formulation expanded under vacuum. The vacuum pressure was then set to −950 mbar. FIG. 3 shows the formulations in the vials at −950 mbar. The 67% filled vial overflowed. The 50% filled vial rose to over the level of the vial. The 10%, 25%, and 33% filled vials all showed about a doubling of volume from the expansion of the air bubbles, but all remained in the vial. Thus, there is a specific range of fill level that can be used at specific vacuum pressures based on the specific properties of the formulation. Since the degassing vessel size is limited, the degassing pressure needs to be adjusted to allow for the product to be degassed in a reasonable time without any overflow of the product. Suitable vacuum for degassing ranges from −300 to −1000 mbar depending the viscosity of the formulations and the size of the degassing vessel.

Example 6: Degassing of a Viscous Formulation

Bubbles are trapped in the formulation during the mixing to solubilize the polymer and bioactive substance. The bulk product needs to be mostly degassed in order to accurately fill the formulation into syringes. In one experiment, a formulation of 8% leuprolide mesylate in a 58% PLGA (IV=0.24) in NMP solution was filled into a vessel until the level was half full. The vessel was then put under vacuum to −900 mbar. The bubbles in the formulation increased in size and the formulation level rose to near the top of the vessel. After 1 hour at −900 mbar, the vacuum was increased to −950 mbar. The formulation then bubbled up and spilled over the side of the vessel.

In another experiment, the vacuum pressure was set at −900 mbar. The bubbles in the formulation increased in size and the formulation level rose to near the top of the vessel. After 1 hour the vacuum was released and the bubble level decreased. The vacuum was reset to −920 mbar and again held for 1 hour. The pressure was then released and the bubble level decreased. The vacuum was then reset to −930 mbar and held for 1 hour. The pressure was then released and the bubble level decreased. The vacuum was then reset to −940 mbar and held for 1 hour. The vacuum was then released and the bubble level decreased. The vacuum was then reset to −950 mbar. The bubble level again rose, but did not overflow. In this way, the formulation can be degassed at a pressure of −950 mbar without any overflow. This procedure can be repeated, progressively increasing the vacuum pressure between each cycle if needed.

Example 7: Vacuum Pressure Range

The level of vacuum pressure was tested in order to determine the optimum range for vacuum. The stronger the vacuum pressure, the faster the degassing, however, the solvent can be removed if the vacuum pressure is too strong. A 50% PLGA/NMP solution was put in a 20 mL glass vial under continuous vacuum. A vacuum pressure of −1013.0 mbar was pulled and the polymer solution was weighed after specified times. Table 1 shows the weight change over time reflecting the loss of NMP due to the vacuum pressure being lower than the vapor pressure of NMP, which is approximately 0.3 mmHg (or relative vacuum −1012.9 mbar).

TABLE 1

| Weight loss of NMP from polymer solution under vacuum | | |
|---|---|---|
| Time (min) | Weight loss (mg) | % loss |
| 5 | 18 | 0.66 |
| 15 | 63 | 2.32 |
| 30 | 105.1 | 3.87 |
| 45 | 156.1 | 5.75 |
| 60 | 180.9 | 6.67 |
| 90 | 279.5 | 10.30 |

In order to reduce the loss of solvent from the formulation, a weaker vacuum can be used, but still high enough to remove the trapped air bubbles.

The formulation degassed in Example 6 was weighed before and after degassing. The weight change was only 0.3%. This is due to the vacuum level used is significantly lower than the vapor pressure of NMP. Thus, a vacuum range was obtained that could degas the formulation, without overflowing the vessel, and without removing the solvent of the composition.

Example 8: Gradient Formation

A formulation of leuprolide mesylate in a PLA (Evonik Resomer Select 100 DL 2E-P (a purified Resomer R 202S), IV 0.22)/NMP solution was compounded and then allocated into 10 mL syringes and connected back to back to an empty 10 mL syringe to allow for product expansion. The syringes were placed in a vacuum of −950 mbar for 3 days to completely degas. One control syringe was left under ambient pressure without degassing. The samples were assayed at top and bottom for leuprolide content. It was found that the average concentration of leuprolide in the top fraction was 10.7%, while the average concentration in the bottom fraction was 11.6%. The control had a leuprolide concentration of 11.4% in the top and 11.5% in the bottom fraction. Thus, during the degassing method of continual vacuum of −950 mbar, unexpectedly, a concentration gradient was formed with a much higher concentration of leuprolide at the bottom of the vessel than at the top.

Example 9: Degassing with Cycles

A formulation of about 10% leuprolide mesylate in about a 58% PLA (Evonik Resomer Select 100 DL 2E-P, IV 0.22) in NMP solution was added to a 50 mL test tube to the 15 mL mark. The tube was placed under vacuum of −950 mbar and the level rose more than double (32 mL). One vessel was kept at −950 mbar, while the other was vented to atmospheric pressure after 1 hour. It was then put back under vacuum at −950 mbar. This vacuum/venting cycling was repeated for a total of 6 cycles. After 3 cycles (3 hours) the level of expansion was reduced to about 17 mL, while the vessel with no cycling was still over 20 mL even after 15 hours. The formulation which was under continuous degassing took over 22 hours to degas, while the formulation which had 6 vacuum/venting cycles took 10 hours to degas. The top and bottom of this vessel were analyzed for leuprolide content. It was unexpected found that the assay at the top, middle, and bottom were very similar indicating there was no formation of a gradient using vacuum/venting degassing cycles. While the formulation which was under continuous degassing showed similar gradient as Example 8 above.

It was unexpected found that not only was the time for degassing was reduced by using cycles of vacuum/venting, the time spent at a high level of expansion (reduced formulation viscosity) was also reduced, and thus the redistribution of leuprolide was prevented. This is important to maintaining the formulation homogeneity during the degassing process.

Example 10: Filtration

After a formulation of leuprolide mesylate in PLA/NMP solution was compounded, half of the formulation was passed through a filter having an average pore size of 100 μm at −950 mbar while the other half was directly placed under a vacuum at −950 mbar to completely degas. After filtering, the formulation was brought to atmospheric pressure and then placed under vacuum at −950 mbar to completely degas. It was found that the formulation that was previously filtered finished degassing in half the time compared to the unfiltered sample. The samples were also assayed for leuprolide content. The filtered sample had a leuprolide concentration of 11.1% in the top and 11.2% in the bottom fractions, while the unfiltered sample had a leuprolide concentration of 10.5% in the top and 11.2% in the bottom fractions. Thus, the filtration step adds another cycle of degassing that can help shorten the degassing time and also reduce leuprolide gradient formation.

Example 11: Filling Following Filtering Under High Vacuum Pressure

The formulations prepared in the previous examples after mixing contain trapped air or gas bubbles. These air bubbles can be compressed under pressure and can be expanded under vacuum. Big air bubbles can be compressed during filling before entering the pump and will expand after passing through the pump due to the release of pressure. Significant product expansion may cause dripping at the filling needle tip resulting in contamination of outside of the syringes and filling weight variation. Therefore, an adequate degree of degassing is necessary. In order to determine what degree of degassing is acceptable for accurate filling, the following experiment was conducted.

7.5 mL of the formulation containing leuprolide as described in Example 8 was filled in one 50 mL centrifuge tube. The tube was put into a vacuum chamber and the vacuum was created to −950 mbar. The product expanded to roughly 18 mL mark. The vacuum was further drawn to −980 mbar and the product expanded past the 50 mL mark. Therefore, from initial to −950 mbar, the product expanded about 2.5-fold. From initial to −980, it was more than 7-fold expansion.

Figure 4:
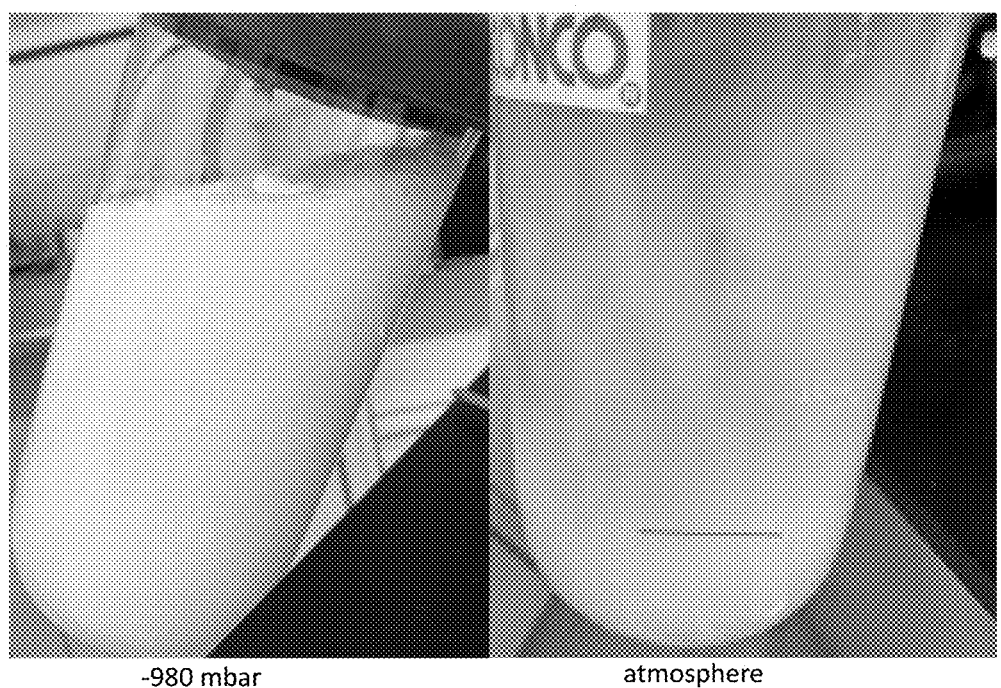
FIG. 4 shows that formulation volume under vacuum at −980 mbar was about four-fold higher than when the formulation was at atmospheric pressure, which indicates that there was a significant amount of bubbles remaining in the formulation based on an embodiment of the present invention.

In order to remove some of the larger bubbles during filtration, the upstream pressure was left at atmospheric and the downstream vacuum pressure was set to −980 mbar. Approximately 450 g of formulation was filtered in about 110 minutes. The formulation still had a lot of trapped bubbles as the volume decreased about 4-fold after turning off the vacuum (FIG. 4). However, the large bubbles appeared to be removed. After the vacuum was turned off, few visible air bubbles in the bulk product could be observed except a few small bubbles on the surface. This degree of degassing may allow the use of the product as is without further degassing to fill syringes.

Over 650 fillings were filled using a semi-automatic filling machine with a rotary piston pump with an inlet pressure of 1.5 bar and a speed of 10 cycles/min and 148 of the filled syringes over this range were weighed. Table 2 shows the average fill weight with standard deviation and relative standard deviation. The filling was just as accurate as when the formulation was completely degassed with the relative standard deviation (RSD) less than 1%. Thus, a significant amount of time can be saved during the manufacturing method by filtering slower under a stronger vacuum downstream, which allows for accurate filling without completely degassing the formulation. The bulk can be majorly degassed with some remaining air bubbles visible at the surface. These results demonstrated that as long as the product expand less than 4-fold under a vacuum pressure of −980 mbar and without visible large air bubbles, no further degassing is necessary to achieve accurate filling.

TABLE 2

| Filling weight of syringes filled without completely degassing formulation | |
| --- | --- |
| AVG | 534.7 mg |
| STD | 3.8 mg |
| RSD | 0.7% |

Example 12: Degassing During Mixing

A double planetary mixer (DPM-Qt) from Ross Mixers was used to make a polymer solution in NMP. Initially, 80% of the NMP was added to the compounding vessel. 25% of the PLA was then added through a side port while using HV stirrer blades at 10 RPM. After the addition, the speed was increased to 30 RPM. The mixing was stopped and another 25% of the polymer was added and the mixing resumed at 30 RPM. After 3 minutes, the powders were all wetted, so the mixing was stopped and the next addition of polymer was made. The mixing was resumed for another 2 minutes to wet the powder. Then the mixing was stopped and another portion of polymer was added to the mixer. This addition was incorporated in about 1 minute. The mixing was stopped again and the final addition of polymer was made. After another minute of mixing at 30 RPM, a vacuum was pulled to approximately -1000 mbar. After 3 minutes, the product was inspected and found that most of the material had dissolved. Mixing was resumed under vacuum, but the compounding vessel was sealed after the vacuum reached the target of -1000 mbar so that there was no loss of NMP. After another 8.5 minutes, the remaining 50 g of NMP was added. The mixing and vacuum were then resumed. After a total of 1 hour, the vessel was opened and a clear uniform solution was obtained of approximately 550 g. The final polymer solution is essentially bubble free.

Example 13: Degassing During Mixing

A double planetary mixer (DPM-2) from Ross Mixers was used to make a polymer solution in NMP. 405 g of NMP (90% of total) was initially added to the compounding vessel. 180 g of polyvinyl pyrrolidone (PVP K30, Avg MW 50 k) (40% of total) was added and mixing started using HV stirrer blades with a bottom cross bar and scraper. The mixer was run at 20 RPM. After 5 minutes, 112.5 g of PVP (25% of total) was added to the compounding vessel. After 5 more minutes, another 112.5 g of PVP was added to the compounding vessel. After another 5 minutes the remaining 45 g of PVP was added to the compounding vessel. The remaining NMP (45 g) was added after another 5 minutes. After a total of 40 minutes of mixing, a vacuum of about -800 mbar was pulled. The material rose in volume. After a couple minutes, the vacuum level was increased to about -950 mbar. After another 40 minutes, the vessel was opened and the product looked translucent with a few remaining air bubbles and no undispersed agglomerates. The product looked very uniform and smooth.

Example 14: Degassing During Mixing for Leuprolide Formulation

In a 6 L compounding vessel, 90% of the NMP (1017.9 g) was introduced first followed by the first fraction of the PLA (Evonik Resomer R 202 S, IV 0.22). The PLA was divided into 4 fractions: 40%, 25%, 25%, 10% of the total amount of the PLA (1529.2 g). The mixing started and a vacuum was pulled to about -300 mbar and held at this level during mixing. The mixing continued for about 30 minutes. The vacuum was then released and the mixing stopped followed by the next addition of PLA. The same process was repeated 4 times until all the fractions of PLA had been added and mixed. Leuprolide mesylate is divided into 3 equal fractions about 33% each. The first fraction of leuprolide mesylate was then added to the vessel and the mixing started. Once the desired mixing speed was reached, the vacuum was pulled to about -300 mbar and held at this level during mixing. The mixing continued for about 15 minutes. The vacuum was then released and mixing stopped followed by the next addition of leuprolide mesylate. The same process was repeated 3 times until all the fractions of leuprolide mesylate had been added and mixed. The vacuum was then increased step wise to -950 mbar through at least 4 cycles of vacuum and venting until reaching a final vacuum pressure of at least -950 mbar while still mixing. The final formulation was a viscous emulsion with few remaining air bubbles.

The resulting formulation was then filtered using a stainless steel mesh having an average pore size of 40 μm to narrow the distribution of Leuprolide/NMP droplet sizes and remove any potential particulate matter or polymer agglomerates in the formulation. The filtration was done under an inlet pressure of 2 bar and an outlet vacuum pressure of -800 mbar. The resulting formulation was a viscous liquid suspension of leuprolide-rich droplets suspended in a PLA-rich continuous phase having a viscosity greater than 10,000 centipoises (cPs). The suspension had few visible trapped air bubbles on the surface of the formulation with a diameter smaller than 5 mm at atmospheric pressure.

Example 15: Mixing Time Effect on Drug Product Uniformity

In a compounding vessel, NMP was introduced first followed by PLA in several fractions until a PLA in NMP solution was obtained. Leuprolide mesylate was then added to a PLA in NMP solution. The solution was mixed for different times and then analyzed for leuprolide/NMP droplet size. To determine the droplet sizes, the formulation was injected into an Ibidi 2-well micro insert on a glass slide and analyzed using an inverted multiphoton confocal scanning microscope with the laser set to 745 nm and the detector at 436-684 nm. Imaging of the droplets was taken at a depth of 10 μm from the surface of the slide to avoid any surface tension effects on the droplets. The images were collected and processed using ImageJ software to calculate the area of the droplets. Table 3 below shows the droplet sizes for these formulations. The size of the droplets and the variability (RSD) of the droplets decreased with increasing mixing time.

TABLE 3

| Effect of Mixing Time on the Droplet Sizes | | | |
| --- | --- | --- | --- |
| LMIS 50 mg Mixing time | Average DV10 (μm) | Average DV50 (μm) | Average DV90 (μm) |
| 5 Minutes | 11.51 ± 17.08 RSD = 148% | 37.96 ± 46.70 RSD = 123% | 68.12 ± 55.79 RSD = 82% |
| 15 Minutes | 4.09 ± 1.69 RSD = 41% | 12.00 ± 9.63 RSD = 80% | 31.20 ± 35.52 RSD = 114% |
| 30 Minutes | 4.93 ± 0.79 RSD = 16% | 14.90 ± 5.84 RSD = 39% | 38.24 ± 22.85 RSD = 60% |

Figure 5:
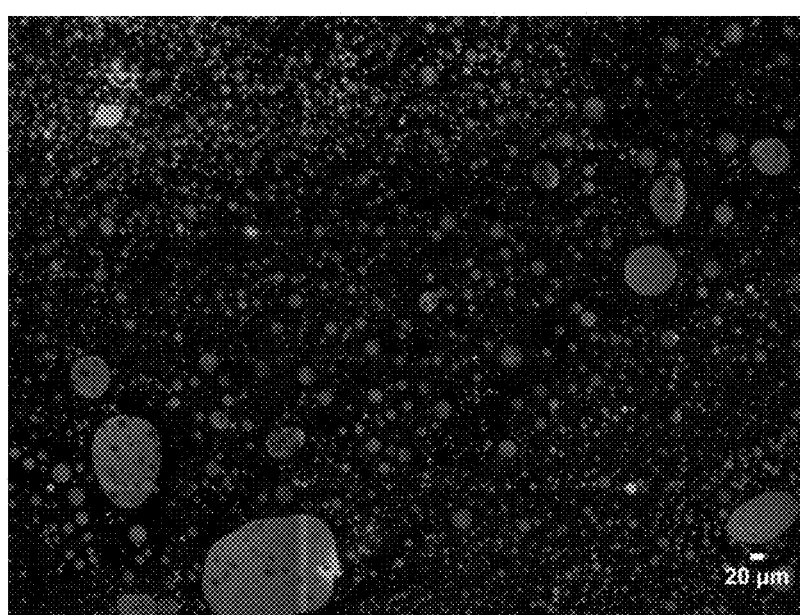
FIG. 5 is an image of leuprolide drug product prepared with incomplete mixing under an inverted confocal microscope. The incomplete mixing leads to a drug product that does not have a uniform particle size and can lead to phase separation.

If the mixing time is not long enough, there will be larger, unstable droplet sizes that can lead to phase separation of the formulation. These larger droplet sizes can be seen under an inverted confocal microscope where the droplet size and distribution can be measured. FIG. 5 shows the confocal image of a formulation that was not mixed completely, leading to larger droplet sizes and an inhomogeneous suspension. Thus, the mixing may be long enough to obtain a uniform homogeneous formulation.

Example 16: Degassing During Mixing for Triptorelin Formulation

Figure 6:
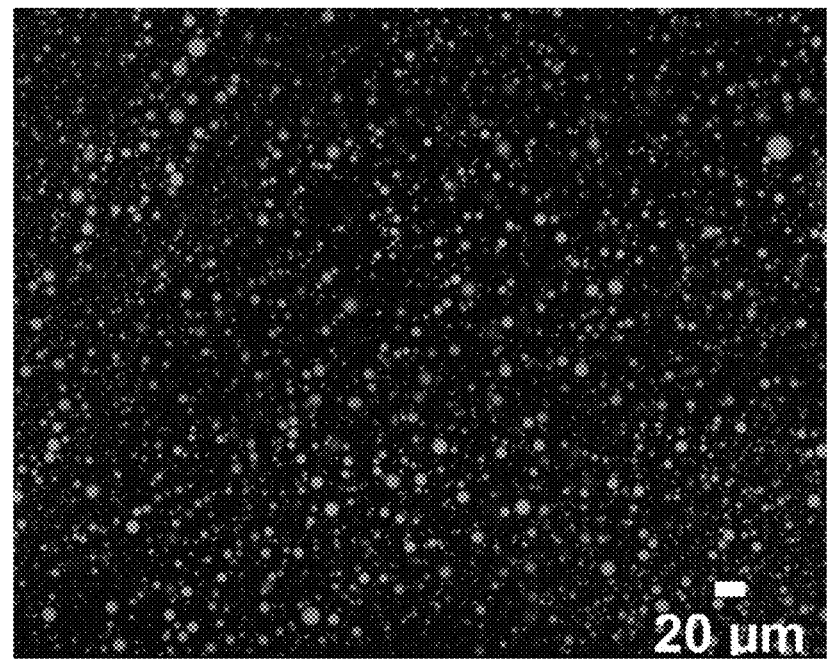
FIG. 6 is an image of a prepared triptorelin drug product viewed under an inverted confocal microscope showing a triptorelin rich phase having droplet sizes less than 20 μm suspended in a polymer rich phase based on an embodiment of the present invention.

In a compounding vessel, a predefined amount of N-methylpyrrolidone and PLA or PLGA was introduced and mixed under vacuum to avoid generating air bubbles. Once the polymers were completely dissolved, a predefined amount of triptorelin mesylate was added and was thoroughly mixed under vacuum until full dissolution to form a viscous suspension without trapped air bubbles or having a few small visible trapped air bubbles with a diameter smaller than 5 mm under atmosphere. The suspension was then filtered using a stainless steel mesh of 20-100 μm size to narrow the distribution of droplet sizes and remove any potential particulate matters or polymer agglomerates in the formulation. The filtration was done under an inlet pressure of 2 bar and an outlet vacuum pressure of −920 mbar. The resulting formulation was a viscous liquid suspension of triptorelin-rich droplets suspended in a PLA-rich or PLGA-rich continuous phase having a viscosity greater than 10,000 centipoises (cPs) as shown in FIG. 6. The suspension only had a few visible trapped air bubbles on the surface of the product with a diameter smaller than 5 mm under atmosphere. The formulation was filled from the tip of the syringe to the desired fill volume to manufacture a single ready to use syringe. Alternatively, the process of claim 1 wherein the formulation is filled from the barrel side of the syringe to the desired fill volume to manufacture a single ready to use syringe.

Example 17: Degassing During Mixing for Goserelin Formulation

Figure 7:
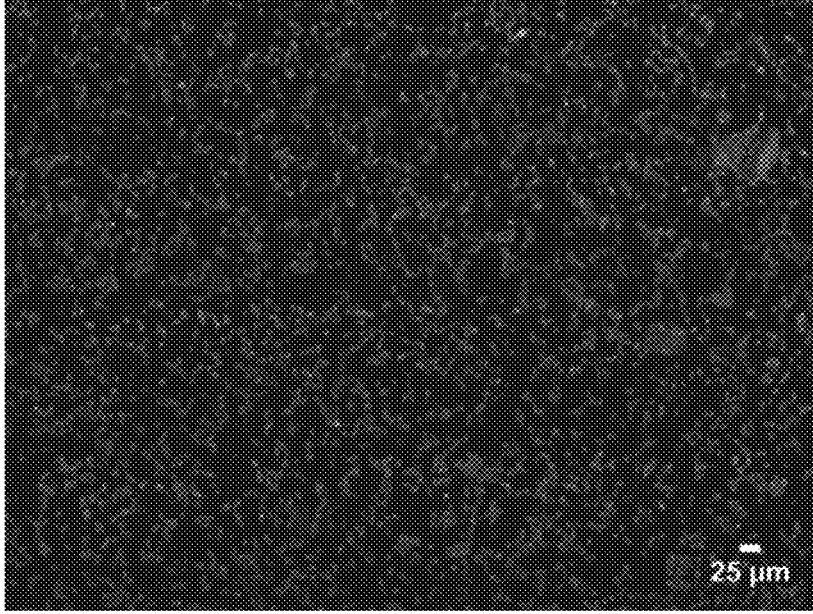
FIG. 7 is an image of goserelin sulphate API viewed under an inverted confocal microscope based on an embodiment of the present invention.

In a compounding vessel, a predefined amount of N-methylpyrrolidone and PLA or PLGA was introduced and mixed under vacuum to avoid generating air bubbles. Once the polymers were completely dissolved, a predefined amount of goserelin sulfate was added and was thoroughly mixed under vacuum until fully wetted to form a viscous suspension without trapped air bubbles or having a few visible trapped air bubbles with a diameter smaller than 5 mm under atmosphere. The resulting formulation was a viscous suspension of goserelin sulfate solid particles suspended in a PLA or PLGA solution in NMP having a viscosity greater than 10,000 centipoises (cPs) as shown in FIG. 7. The suspension only had a few visible trapped air bubbles on the surface of the products with a diameter smaller than 5 mm under atmosphere. The formulation was filled from the tip or from the barrel side of the syringe to the desired fill volume to manufacture a single ready to use syringe.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present inventions as defined by the specific description.

What is claimed:

1. A method of manufacturing an injectable sustained release formulation, wherein the injectable sustained release formulation comprises a luteinizing hormone releasing hormone (LHRH) agonist or a salt thereof, an N-methylpyrrolidone (NMP), and a biodegradable polymer, and wherein the method comprises:

i. a compounding step that is conducted under a controlled humidity of less than 60% at 15-25° C., wherein the compounding step comprises a) introducing ≥70% of a total amount of the NMP into a compounding vessel; b) dividing the biodegradable polymer into multiple fractions and adding a first fraction of the biodegradable polymer to the compounding vessel, and mixing the first fraction of the biodegradable polymer with the NMP in the compounding vessel until the first fraction of the biodegradable polymer is wetted or dissolved, then separately and sequentially introducing each of the remaining fraction(s) of the biodegradable polymer to the compounding vessel and mixing until the newly added fraction of the biodegradable polymer is wetted or dissolved before introducing a next fraction of the biodegradable polymer; c) after all the fractions of the biodegradable polymer are wetted or dissolved, adding the LHRH agonist in 1 to 20 fractions separately and sequentially into the compounding vessel and mixing the fraction of LHRH agonist with the NMP and biodegradable polymer in the compounding vessel until the LHRH agonist is wetted or dissolved, wherein a subsequent fraction of the LHRH agonist, if any, is added after the LHRH agonist previously added into the compounding vessel is wetted or dissolved, and mixing the LHRH agonist with the NMP and biodegradable polymer in the compounding vessel to form the formulation; and ii. a degassing step that is performed by four (4) or more vacuum/vent cycles of applying a relative vacuum pressure between −300 mbar and −1000 mbar to the compounding vessel or a degassing vessel containing the formulation prepared in (i) above, maintaining the vacuum for a time period between 5 min and 720 min, and releasing the vacuum to allow venting; wherein the vacuum level maintained at each vacuum/vent cycle is at least as strong as or stronger than that maintained in an immediately previous cycle, wherein the formulation is a viscous suspension or emulsion of LHRH agonist rich phase having a droplet diameter of Dv50 of less than 50 pm suspended in a biodegradable polymer rich continuous phase and has a viscosity of greater than 10,000 centipoise (cPs).

2. The method of claim 1 wherein after the last fraction of LHRH agonist is introduced, the formulation is further mixed for at least 15 minutes to obtain LHRH/NMP droplets in the formulation having a droplet size of Dv50≤25 μm with an RSD≤100%.

3. The method of claim 1 wherein the LHRH agonist is leuprolide mesylate or triptorelin mesylate.

4. The method of claim 1 wherein the biodegradable polymer is selected from the group consisting of polylactic acid (PLA), and a copolymer poly (lactic acid-co-glycolic acid) (PLGA), and a combination thereof, wherein the ratio of lactic acid:glycolic acid of the copolymer is from 50:50 to 99:1; wherein the PLGA or PLA polymer has a molecular weight from 5,000-50,000 dalton.

5. The method of claim 1 wherein the compounding step is performed under a controlled humidity of less than or equal to 40% at 15-25° C.

6. The method of claim 1 wherein 70-90% of the total NMP is introduced to the compounding vessel initially, with remaining 10-30% being introduced after the adding of all the biodegradable polymer and LHRH agonist.

7. The method of claim 1 wherein the LHRH agonist is added to the compounding vessel all at once and dissolved.

8. The method of claim 1 where the LHRH agonist is added to the compounding vessel in 2 or more fractions separately and sequentially and dissolved, and the subsequent fraction of the LHRH agonist is added after the LHRH agonist previously added in the compounding vessel is dissolved.

9. The method of claim 1 further comprises performing a filtration step using a filter having average pore sizes ranging from 20 μm to 100 μm under an inlet pressure of 1 bar to 10 bars and an outlet relative vacuum pressure of −300 mbar to −1000 mbar, wherein the filtration is performed before the degassing step.

10. The method of claim 9 wherein the filter has an average pore size of 40 μm, and the filtration is performed under an inlet pressure of 1.8 to 2.0 bars and an outlet relative vacuum pressure of −700 mbar to −950 mbar.

11. The method of claim 1 wherein the suspension or emulsion is substantially air bubble free and homogeneous.

12. The method of claim 1 wherein the LHRH agonist is triptorelin mesylate and the biodegradable polymer is PLA or PLGA.

\*   \*   \*   \*   \*